(12) United States Patent
Li et al.

(10) Patent No.: US 7,253,909 B1
(45) Date of Patent: *Aug. 7, 2007

(54) PHASE SHIFT MEASUREMENT USING TRANSMITTANCE SPECTRA

(75) Inventors: Guoguang Li, Fremont, CA (US);
Phillip Walsh, San Jose, CA (US);
Shuqiang Chen, Sunnyvale, CA (US);
Abdul Rahim Forouhi, Cupertino, CA (US)

(73) Assignee: n&k Technology, Inc., Santa Clara, CA (US)

( * ) Notice: Subject to any disclaimer, the term of this patent is extended or adjusted under 35 U.S.C. 154(b) by 289 days.

This patent is subject to a terminal disclaimer.

(21) Appl. No.: 11/028,894

(22) Filed: Jan. 3, 2005

Related U.S. Application Data

(63) Continuation-in-part of application No. 10/607,410, filed on Jun. 25, 2003, now Pat. No. 6,891,628.

(51) Int. Cl.
*G01B 11/00* (2006.01)
(52) U.S. Cl. ........................ 356/625; 356/636
(58) Field of Classification Search ................ 356/625, 356/632, 636, 237.5, 369
See application file for complete search history.

(56) References Cited

U.S. PATENT DOCUMENTS

| | | | |
|---|---|---|---|
| 4,757,207 A | 7/1988 | Chappelow et al. | 250/491.1 |
| 4,850,711 A * | 7/1989 | Sano et al. | 356/632 |
| 4,866,782 A | 9/1989 | Sugie et al. | 382/22 |
| 5,061,072 A * | 10/1991 | Folkard et al. | 356/369 |
| 5,087,121 A | 2/1992 | Kakuchi et al. | 356/73 |
| 5,184,021 A | 2/1993 | Smith | 250/560 |
| 5,363,171 A | 11/1994 | Mack | 355/68 |
| 5,392,116 A | 2/1995 | Makosch | 356/351 |
| 5,452,091 A * | 9/1995 | Johnson | 356/445 |
| 5,604,591 A | 2/1997 | Kitagawa | 356/351 |
| 5,607,800 A | 3/1997 | Ziger | 430/8 |
| 5,739,909 A | 4/1998 | Blayo et al. | 356/369 |
| 5,867,276 A | 2/1999 | McNeil et al. | 356/455 |
| 5,963,329 A | 10/1999 | Conrad et al. | 356/372 |
| 6,122,056 A | 9/2000 | Hibbs et al. | 356/345 |
| 6,340,602 B1 | 1/2002 | Johnson et al. | 438/7 |
| 6,426,644 B1 * | 7/2002 | Borden et al. | 356/445 |
| 6,483,580 B1 | 11/2002 | Xu et al. | 356/300 |

OTHER PUBLICATIONS

Chopra, K.L., Thin Film Phenomena, pp. 99-105 (McGraw Hill).
Cynthia B. Brooks, et al., "Process Monitoring of Etched Fused Silica Phase Shift Reticles", Proceedings of the SPI, 22nd Annual BACUS Symposium of Technology and Management, Sep. 30-Oct. 4, 2002, Monterey, CA, USA.
Alessandro Callegari and Katerina Babich, "Optical Characterization of Attenuated Phase Shifter", SPIE, vol. 3050, pp. 507-514.
Pieter Burggraff, "Litography's Leading Edge, Part 1: Phase Shift Technology", Feb. 1992, pp. 43-47.
Hal Kusunose et al., "Development of Phase-shift and Transmittance Metrology System for 157 nm PSMs," Proceedings of SPIE vol. 5256, pp. 628-637.

* cited by examiner

*Primary Examiner*—Richard A. Rosenberger
(74) *Attorney, Agent, or Firm*—Lumen Intellectual Property Services, Inc.

(57) ABSTRACT

An apparatus and method for determining a physical parameter of features on a substrate by illuminating the substrate with an incident light covering an incident wavelength range $\Delta\lambda$, e.g., from 190 nm to 1000 nm, where the substrate is at least semi-transparent. A response light received from the substrate and the feature is measured to obtain a response spectrum of the response light. Further, a complex-valued response due to the feature and the substrate is computed and both the response spectrum and the complex-valued response are used in determining the physical parameter. A direct approximate phase measurement is provided when the response light is transmitted light.

24 Claims, 16 Drawing Sheets

PHASE SHIFT MEASUREMENT USING TRANSMITTANCE SPECTRA

CROSS REFERENCE TO RELATED APPLICATIONS

This application is a continuation-in-part of application Ser. No. 10/607,410 filed on Jun. 25, 2003 now U.S. Pat. No. 6,891,628 and entitled "Method and Apparatus for Examining Features on Semi-Transparent and Transparent Substrates".

FIELD OF THE INVENTION

The present invention relates generally to methods and apparatus for optically examining features on semi-transparent substrates and especially to examining a number of adjacent features on such semi-transparent substrates.

BACKGROUND OF THE INVENTION

In the production of miniaturized objects such as miniature devices including integrated circuits and microelectronics for semiconductor and display applications, the tools and auxiliary structures used in their manufacture, as well as the miniature objects themselves have to be examined carefully. Optical methods of examining these tools and objects are non-destructive and frequently preferred over other approaches. Hence, advances in optical examination of miniature features including patterns composed of adjacent features are important.

In many cases miniature devices are made by photolithographic techniques. In a typical application of the photolithographic technique, a layer of photoresist is deposited on a substrate or other device layer and then exposed to radiation of appropriate wavelength through a patterning mask. Of course, the masks themselves also need to be appropriately patterned with miniature features to be able to perform their function and are thus themselves a class of miniature devices that has to be examined.

Now in photolithography certain regions of the photoresist layer are exposed and others are not, according to the pattern defined in the patterning mask. Exposing the photoresist to radiation changes its solubility. After exposure, solvent is used to remove regions of higher solubility photoresist, leaving regions of "hardened" photoresist at sites on the device layer as dictated by the patterning mask. The "hardened" photoresist remains to protect the underlying material from removal during a subsequent etching step or other suitable material removal procedure. After etching the photoresist is discarded. In this manner, a feature is created in the device based on the pattern defined in the mask.

Clearly, the photoresist layer must be accurately patterned to form features to the exacting specifications for miniature devices. It is therefore desirable to monitor the photolithographic process at various stages and on a periodic basis. For example, it would be desirable to measure the thickness of the photoresist layer and examine the pattern to determine feature sizes. The thickness can be measured by subjecting the photoresist to light with a wavelength in the range of 190 to 1000 nm and measuring the reflected light. The reflected radiation may be correlated to photoresist thickness. The general principle of this measurement technique is that the measured light reflected from a substrate is modulated by constructive and destructive optical interference from an overlaying semitransparent material such as the photoresist. For more information see Chopra, K. L., *Thin Film Phenomena*, p. 99 (McGraw Hill, 1969). The periodicity of the reflectance spectra can also be used to determine optical properties, such as the refractive index n of the substrate.

Measurement of the pattern or features is a more difficult procedure. For example, in a typical application, the pattern consists of a plurality of stripes and spaces, e.g., a line and space pattern. These types of patterns are frequently encountered in forming diffractive elements such as lenses or gratings in semiconductors or glass, forming fluid flow microchannels in silicon, and in general for providing a variety of mechanical features in a substrate. In measuring stripe widths and separations the prior art techniques have typically relied on scanning electron microscopy (SEM). Unfortunately, SEM is a destructive and very time-consuming examination method.

Methods such as atomic force microscopy (AFM) and profilometry are also viable for examining features or patterns of features. However, both of these methods are very time consuming and they require special test structures in most cases.

The patterning masks used to create resist lines often themselves contain features. Of particular interest are Alternating Phase Shift Masks (AAPSMs), which are often quartz or fused silica plates etched with trenches in repeating patterns. This creates an interference condition between light passing through the etched and un-etched regions of the mask, leading to complete amplitude cancellation in regions that would normally have been exposed. In this way an AAPSM can be used to pattern features in the resist that are smaller than the wavelength of light used to expose the resist. Accurate metrology control of the dimensions of these features is critical, since in a typical application using 248 nm wavelength light, approximately 13 Å difference in trench depth is enough to change the phase shift by 1 degree.

In addition to AFM, SEM, and profilometry the prior art offers interferometric techniques for measuring high-precision patterns, such as those encountered in AAPSMs. Unfortunately, because of the inherent limitations of AFM, SEM and profilometry already mentioned, these techniques are not satisfactory for examining AAPSMs. Interferometric techniques are too expensive, and require special test structures. Furthermore, the test features have to be large enough so that reference and measurement beams can be fully covered by two different uniform areas respectively. These test features often do not reflect the phase shift characteristics of the features to be printed on the mask. In addition, in most cases the test features have to be transparent. This condition prevents the measurement from being performed at the early stages of mask processing when an opaque metallic layer, such as Cr, is frequently present.

For more information on AAPSMs and methods for examining them the reader is referred to Cynthia B. Brooks, et al., "Process Monitoring of Etched Fused Silica Phase Shift Reticles", Proceedings of the SPIE, 22$^{nd}$ Annual BACUS Symposium on Photomask Technology and Management, Sep. 30-Oct. 4, 2002, Monterey, Calif., USA; Alessandro Callegari and Katherina Babich, "Optical Characterization of Attenuated Phase Shifters", SPIE, Vol. 3050, pp. 507-514; as well as Pieter Burggraaf, "Lithography's Leading Edge, Part I: Phase Shift Technology", Feb. 1992, pp. 43-47.

More recently, attempts have been made to measure patterns using scatterometry. In this technique, a pattern is subjected to light, such as from a laser, typically having a single wavelength. This light is usually directed toward the pattern at some angle to the normal. The light reflected from the pattern at various diffracted orders is measured. It may be possible to use such data to obtain quantitative information about the pattern. However, scatterometry is very sensitive to small changes in the profile of the pattern, and requires relatively sophisticated correlation work to relate the reflected radiation to the features of a pattern. The computational effort required to correlate the reflected radiation to the pattern is very high since the convergence criteria for these solutions take a very long time to compute. In addition, the measured pattern must be periodic. Other examples of characterization methods pertaining to photolithography and equipment suitable for practicing such methods are described in U.S. Pat. Nos. 5,867,276; 5,363,171; 5,184,021; 4,866,782 and 4,757,207. There are still other types of scatterometry, which measure the specularly reflected light as a function of wavelength, as taught in U.S. Pat. Nos. 6,483,580; 5,963,329; 5,739,909 and 5,607,800.

Of these references U.S. Pat. No. 5,607,800 to Ziger teaches a method and arrangement for characterizing features of a patterned material on an underlayer. His approach is based on selecting an appropriate wavelength range where the patterned material absorbs more radiation than the underlayer. In other words, substrate or underlayer is more reflective than the pattern or surface features in this wavelength range. The reflectance spectrum uniquely identifies the pattern and can be used to study similar patterns by comparing their reflectance spectra. Unfortunately, just as in the case of scatterometry, when patterns vary this comparison-based approach can not be used effectively to study patterns which differ substantially from each other.

U.S. Pat. No. 6,100,985 to Scheiner et al. teaches a method for measuring at least one desired parameter of a patterned structure having a plurality of features. In this method a measurement area, which is substantially larger than a surface area of the structure defined by the grid cycle, is illuminated by an incident radiation of a preset substantially wide wavelength range. The light component that is substantially specularly reflected from the measurement area is detected, and measured data representative of photometric intensities of each wavelength within the wavelength range is obtained. The measured and theoretical data are analyzed and the optical model is optimized until the theoretical data satisfies a predetermined condition. Upon detecting that the predetermined condition is satisfied at least one parameter of the structure is can be calculated.

A still more recent teaching for optically determining a physical parameter of a pattern made up of features is taught in U.S. Pat. No. 6,327,035 to Li et al. This teaching goes further than Scheiner et al. by examining various response light fractions including an underlayer light fraction and a feature light fraction and using reference physical parameters of the underlayer. The response light can be either transmitted or reflected and the reference physical parameters of the underlayer are either known a priori or determined.

U.S. Pat. No. 6,340,602 to Johnson et al. teaches a method for measuring a parameter associated with a portion of a sample having one or more structures with at least two zones each having an associated zone reflectance property. The at least two zones are illuminated with broadband light, the reflected light is measured and a measured reflectance property is fit to a model. The model mixes the zone reflectance properties to account for partially coherent light interactions between the two zones.

Although Johnson's approach attempts to address coherence issues between the zones, it does not take into account the interactions between the broadband light and the substrate. More precisely, in this approach the substrate is assumed to be opaque and only lateral incoherence between the zones themselves is treated. In most cases, however, substrates on which features or zones are measured are at least partially transparent over a portion or even the entire broadband spectrum of the incident broadband light. Thus, by leaving out the complex interactions between the illuminating light, the zones and the substrate, Johnson is not able to provide a method that can be used for measuring zones or features on semi-transparent and transparent substrates.

In fact, the problem of optically examining features and patterns on underlayers or substrates that are at least semi-transparent or fully transparent has eluded a satisfactory solution because of its complexity. This complexity is partly due to the large series of internal reflections and transmissions affecting the response light obtained from the substrate and features. What is more, the response light is not only conditioned by the multiple internal reflections and transmissions within the substrate and features to be examined, but also by coherent and incoherent interactions between reflected and/or transmitted response light from the substrate and the various features.

OBJECTS AND ADVANTAGES

In view of the above, it is a primary object of the present invention to provide a method and apparatus that enables a thorough optical examination of features on semi-transparent and even transparent substrates. More specifically, it is an object of the present invention to provide a method of examining the response light in a manner which takes into account the coherent and incoherent interactions between reflected and/or transmitted response light within and among various features.

Another object of the invention is to provide direct measurement of transmission phase shift without requiring detailed modeling and/or analysis of measured results.

These and numerous other objects and advantages of the present invention will become apparent upon reading the following description.

SUMMARY

The objects and advantages of the present invention are secured by a method for determining a physical parameter of features on a substrate by illuminating the substrate with an incident light covering an incident wavelength range $\Delta\lambda$ where the substrate is at least semi-transparent and such that the incident light enters the substrate and the features. A response light received from the substrate and the features is measured to obtain a response spectrum of the response light. Further, a complex-valued response due to the features and the substrate is computed and both the response spectrum and the complex-valued response are used in determining the physical parameter. This physical parameter can be a depth, a width, a real part of the complex refractive index, an imaginary part of the complex refractive index or some other physical parameter of the features.

The response light is reflected light, transmitted light or a combination of the two and it can be either polarized or unpolarized. Thus, the response spectrum corresponds to either a reflectance R, a transmittance T or both. The complex-valued response typically includes a complex reflectance amplitude, a complex transmittance amplitude or both. In accordance with the method of invention, when the complex-valued response is or includes the complex reflectance amplitude the reflectance R is computed by multiplying the complex reflectance amplitude with its complex conjugate. Similarly, when the complex-valued response is or includes the complex transmittance amplitude the transmittance T is computed by multiplying the complex transmittance amplitude with its complex conjugate.

A vertical coherence length $L_{vc}$ of the incident light and thickness $d_s$ of the substrate determine whether the response light is coherent or incoherent. For example, when the vertical coherence length $L_{vc}$ is small with respect to thickness $d_s$ then the response light exhibits incoherence. In such cases a phase $\delta_s$ of the complex-valued response is averaged in the computation.

The method of invention is particularly advantageous when the features are adjacent. In most such cases the wavelength range $\Delta\lambda$ is selected such that the substrate and the adjacent features produce a coherent fraction and an incoherent fraction in the response light. Preferably, further computations are made to determine a coherent fraction $\beta$ (or coherent factor) for coherent adding of the complex-valued response. An incoherent fraction of the response light is equal to $1-\beta$. The coherent fraction $\beta$ can be determined from a lateral coherence length $L_{lc}$ of the incident light. It should be noted that this approach presents a closed-form solution to determining the complex-valued response of adjacent features on a substrate.

In cases where the features are periodic the incident light will experience diffraction. Thus, when the features are periodic it is preferable to focus the incident light to an illumination area covering a sufficiently small number of features such that diffraction effects are negligible.

When the area of the features is larger than the lateral coherence length $L_{lc}$ of the incident light then the complex-valued response from the features is added incoherently. Otherwise, when the area of at least one of the features is smaller than the lateral coherence length $L_{lc}$ then the complex-valued response is added coherently. It should be noted that lateral coherence length $L_{lc}$ as well as vertical coherence length $L_{vc}$ are wavelength dependent.

The features can be adjacent features made of two different materials, such as material 1 covering a first area fraction $a_1$ and material 2 covering a second area fraction $a_2$. The area fractions $a_1$ and $a_2$ correspond to the fractional area illuminated by the incident light. Depending on the embodiment, the complex-valued response to be added coherently is a total complex-valued reflectance amplitude $r_C$, a total complex-valued transmittance amplitude $t_C$ or both. The following equations are used in the computations:

$$r_C = a_1 r_1 + a_2 r_2,$$

$$t_C = a_1 t_1 + a_2 t_2, \text{ and}$$

$$a_1 + a_2 = 1.$$

The response spectra such as a coherent reflectance $R_C$ and coherent transmittance $T_C$ are then computed by multiplying out the complex-valued amplitudes by their complex conjugates. In particular, coherent reflectance $R_C$ is computed by using the following cross term:

$$\langle r_1 \cdot r_2^* \rangle = \frac{r_{1,as} r_{2,as}^* + (t_{1,as} t_{2,as}^* t_{1,sa} t_{2,sa}^* - r_{1,as} r_{2,as}^* r_{2,sa} r_{2,sa}^*) r_{1,sb} r_{2,sb}^* e^{-2\alpha_s d_s}}{1 - r_{1,sa} r_{2,sa}^* r_{1,sb} r_{2,sb}^* e^{-2\alpha_s d_s}},$$

where $\alpha_s$ is an absorption coefficient of the substrate and $d_s$ is the thickness of the substrate. In embodiments where the incident light is focused on a back side of the substrate, the cross term simplifies and is computed as:

$$\langle r_1 \cdot r_2^* \rangle = t_{1,as} t_{2,as}^* t_{1,sa} t_{2,sa}^* r_{1,sb} r_{2,sb}^* e^{-2\alpha_s d_s}.$$

Meanwhile, coherent transmittance $T_C$ is calculated by using the following cross term:

$$\langle t_1 \cdot t_2^* \rangle = \frac{t_{1,as} t_{2,as}^* t_{1,sb} t_{2,sb}^* e^{-\alpha_s d_s}}{1 - r_{1,sa} r_{2,sa}^* r_{1,sb} r_{2,sb}^* e^{-2\alpha_s d_s}} = A e^{i\phi},$$

where A is the amplitude of $\langle t_1 \cdot t_2^* \rangle$, $\phi$ is the phase shift between $t_1$ and $t_2$. As before, $\alpha_s$ is the absorption coefficient and $d_s$ is the thickness of the substrate.

The method of invention can be practiced under various illumination conditions. In one embodiment the incident light is collimated. In another embodiment, the incident light is focused. For example, the incident light is focused on a surface of the substrate. The substrate can be illuminated from a first side where the feature or features are located or from a side opposite the first side. It should also be noted that the incident light can be linearly polarized.

In certain applications of the method the physical parameter is derived from phase shift $\phi$ or amplitude A of the response light. In other words, phase shift $\phi$ and/or variation of amplitude A experienced by reflected and/or transmitted response light is used to determine the physical parameter of the features. In some embodiments, information about physical parameters of the features is derived from phase shift $\phi$. Specifically, in embodiments where the response light is transmitted the phase shift $\phi$ can be obtained from:

$$\phi = \phi_T = \frac{2\pi(n\cos\theta_2 - \cos\theta_1)t_s}{\lambda}.$$

In embodiments where the response light is reflected the phase shift $\phi$ can be obtained from:

$$\phi = \phi_R = \frac{4\pi n t_s \cos\theta_2}{\lambda}.$$

In the preferred embodiment where at least two adjacent features are being examined the incident light enters the substrate and the features and the complex-valued response exhibits interference due to the features. The interference manifests in phase $\phi$ observed in the measured response light. In order to examine these variations it is convenient to examine a wide reflectance R and/or transmittance T spectrum, e.g., from about 190 nm to about 1000 nm.

The method of invention can be used to determine physical parameters of features in various arrangements. For example, at least one of the features can be in the form of a film, e.g., a flat film. One or more additional features can be embedded in the film.

The invention further extends to an apparatus for determining a physical parameter of one or more features on a substrate. The apparatus has an illumination source for producing the incident light and optics for guiding the incident light such that the incident light enters the substrate and the features. A detector is provided for receiving the response light and measuring its response spectrum. In addition, the apparatus has a processing unit for computing the complex-valued response of the substrate and the one or more features and determining the physical parameter from the measured response spectrum and the complex-valued response.

The substrate can be transparent within the incident wavelength range Δλ or optically thick. In practice, the substrate will exhibit a variation in its degree of transparency over the selected wavelength range Δλ. In some cases, the substrate can be optically thick over a large portion of the entire wavelength range Δλ, e.g., when the substrate comprises a metal layer. In a preferred embodiment the apparatus examines a wide wavelength range Δλ by providing an illumination source that is broadband. In one embodiment the broadband illumination source provides an incident wavelength range Δλ from about 190 nm to about 1000 nm.

A detailed description of the invention and the preferred and alternative embodiments is presented below in reference to the attached drawing figures.

THEORETICAL BACKGROUND

Figure 1:
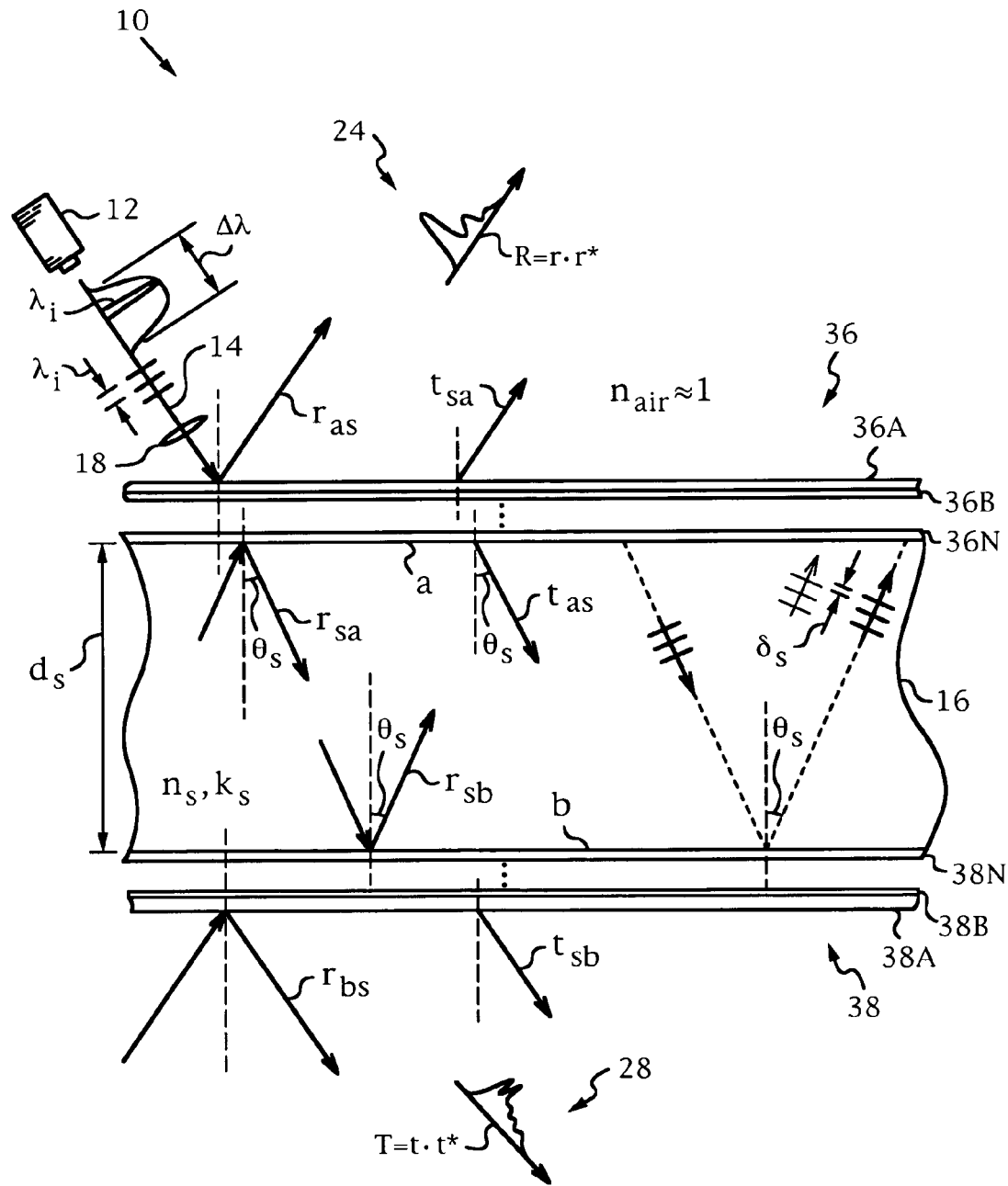
FIG. 1 (PRIOR ART) is a schematic diagram illustrating some optics principles on which the invention is based.

The instant invention will be best understood by first considering the prior art schematic diagram of FIG. 1 illustrating some optics principles. Apparatus 10 has an illumination source 12 that generates an incident light 14 spanning an incident wavelength range Δλ. Source 12 is positioned to illuminate a substrate 16 with incident light 14. Optics 18 are positioned to guide incident light 14 from source 12 to substrate 16.

Substrate 16 has a thickness $d_s$ typically on the order of a fraction of a millimeter to several millimeters, e.g., 0.2 mm to 8 mm. Substrate 16 can be made of any material that is semi-transparent within an incident wavelength range Δλ covered by incident light 14. The material of substrate 16 is optically described by a real part $n_s$ and imaginary part $k_s$ of the complex refractive index. For example, the material of substrate 16 can be diffused silica or glass.

Substrate 16 has a stack of films 36 on a first side a and a stack of films 38 on a second side b. Stack 36 can include a large number of films 36A, 36B, . . . 36N. Likewise, stack 38 can include a large number of films 38A, 38B, . . . 38N.

Incident light 14 enters substrate 16 through stack 36 deposited on a side a of substrate 16. It should be noted that films 36 can have any structure and composition and represent features. Now, when incident light 14 enters substrate 16 from side a two complex-valued responses due to substrate 16 and stacks 36, 38 are produced. The first complex-valued response is a complex reflectance amplitude r and the second complex-valued response is a complex transmittance amplitude t, given by:

$$r = \frac{r_{as} + (t_{as}t_{sa} - r_{as}r_{sa})r_{sb}e^{-i\delta_s - \alpha_s d_s}}{1 - r_{sa}r_{sb}e^{-i\delta_s - \alpha_s d_s}}, \quad \text{Eq. 1}$$

$$t = \frac{t_{as}t_{sb}e^{-(i\delta_s + \alpha_s d_s)/2}}{1 - r_{sa}r_{sb}e^{-i\delta_s - \alpha_s d_s}}. \quad \text{Eq. 2}$$

In these equations $\delta_s$ is the phase and $\alpha_s$ is the absorption coefficient given by:

$$\delta_s = \frac{4\pi n_s d_s \cos\theta_s}{\lambda}, \qquad \text{Eq. 3}$$

$$\alpha_s = \frac{4\pi k_s \cos\theta_s}{\lambda}. \qquad \text{Eq. 4}$$

In these equations "a" denotes side a, "b" denotes side b, s denotes substrate 16, $d_s$ is the thickness of substrate 16, $n_s$, $k_s$ are the real and imaginary parts of the complex refractive index of substrate 16 and $\theta_s$ is the incident angle of light 14 inside substrate 16. Coefficients $r_{uv}$ and $t_{uv}$ (u,v=a,b,s) are the reflection and transmission coefficients. For example, $t_{as}$ is the transmission coefficient from the atmosphere surrounding substrate 16, in this case air, through stack 36 on side a to substrate 16, and $t_{sa}$ is the transmission coefficient from substrate 16 through stack 36 on side a to air. The analytical expressions for $r_{uv}$ and $t_{uv}$ are well known and can be found in standard textbooks, such as O. S. Heavens, *Optical Properties of Thin Solid Films*, Dover, Chapter 4. It should be noted that these equations are valid for both s- and p-polarized light.

In response to incident light 14 substrate 16 and stacks of films 36, 38 generate response light. The response light includes both reflected light 24 and transmitted light 28. The response spectrum of reflected light 24 detected by detector 26 is obtained by multiplying complex reflectance amplitude r by its complex conjugate r*. This multiplication yields a reflectance R:

$$R = r \cdot r^*. \qquad \text{Eq. 5}$$

Similarly, the response spectrum of transmitted light 28 detected by detector 30 is described by a transmittance T. Transmittance T is obtained by multiplying complex transmittance amplitude t by its complex conjugate t* as follows:

$$T = t \cdot t^*. \qquad \text{Eq. 6}$$

The choice of range $\Delta\lambda$ of incident light 14 is such that substrate 16 is semi-transparent or even transparent at any particular wavelength, e.g., at $\lambda_i$, within range $\Delta\lambda$. Therefore, at a particular wavelength, e.g., at $\lambda_i$, response light 24, 28 undergoes multiple internal reflections and transmissions before emerging from substrate 16.

Depending on a vertical coherence length $L_{vc}$ of light 14 response light 24, 28 is coherent or incoherent. More precisely, when vertical coherence length $L_{vc}$ is sufficiently small with respect to thickness $d_s$ of substrate 16 then response light 24, 28 exhibits incoherence. This is visualized in FIG. 1 for response light 24, 28 at wavelength $\lambda_i$ by showing a "slip-off" in phase $\delta_s$ produced after several internal reflections. For a source 12 with 2 nm line width (which gives vertical coherence length $L_{vc}$~0.1 mm at 500 nm) and thickness $d_s$ larger than 0.2 mm response light 24, 28 undergoes multiple reflections within substrate 16 and exhibits incoherence.

When response light 24, 28 exhibits incoherence then phase $\delta_s$ of the complex-valued responses, i.e., complex reflectance and transmission amplitudes r, t needs to be averaged. Averaging of phase $\delta_s$ yields the following reflectance R and transmittance T:

$$R = \frac{1}{2\pi}\int_0^{2\pi} r \cdot r * d\delta_s, \text{ or} \qquad \text{Eq. 7}$$

$$= \frac{r_{as}r_{as}^* + (t_{as}t_{as}^* t_{sa}t_{sa}^* - r_{as}r_{as}^* r_{sa}r_{sa}^*)r_{sb}r_{sb}^* e^{-2\alpha_s d_s}}{1 - r_{sa}r_{sa}^* r_{sb}r_{sb}^* e^{-2\alpha_s d_s}},$$

$$T = \frac{1}{2\pi}\int_0^{2\pi} t \cdot t * d\delta_s, \text{ or} \qquad \text{Eq. 8}$$

$$= \frac{t_{as}t_{as}^* t_{sb}t_{sb}^* e^{-\alpha_s d_s}}{1 - r_{sa}r_{sa}^* r_{sb}r_{sb}^* e^{-2\alpha_s d_s}}.$$

The response spectra, in this case reflectance R and transmittance T, account for the complex-valued transmittance and reflectance amplitudes r, t due to substrate 16 and stacks 36, 38.

DETAILED DESCRIPTION OF THE EMBODIMENTS

The method of invention is based on the fact that knowledge of materials making up films 36, 38 and substrate 16, as well as their physical dimensions yield the information necessary to compute complex-valued reflectance and transmittance amplitudes r, t. Therefore, in practicing the method of invention the complex-valued response due to the features such as films 36, 38 and substrate 16 has to be known before measurement. The computed complex-valued response is used in determining one or more physical parameters of one or more of films 36, 38 actually being examined on substrate 16.

Figure 2:
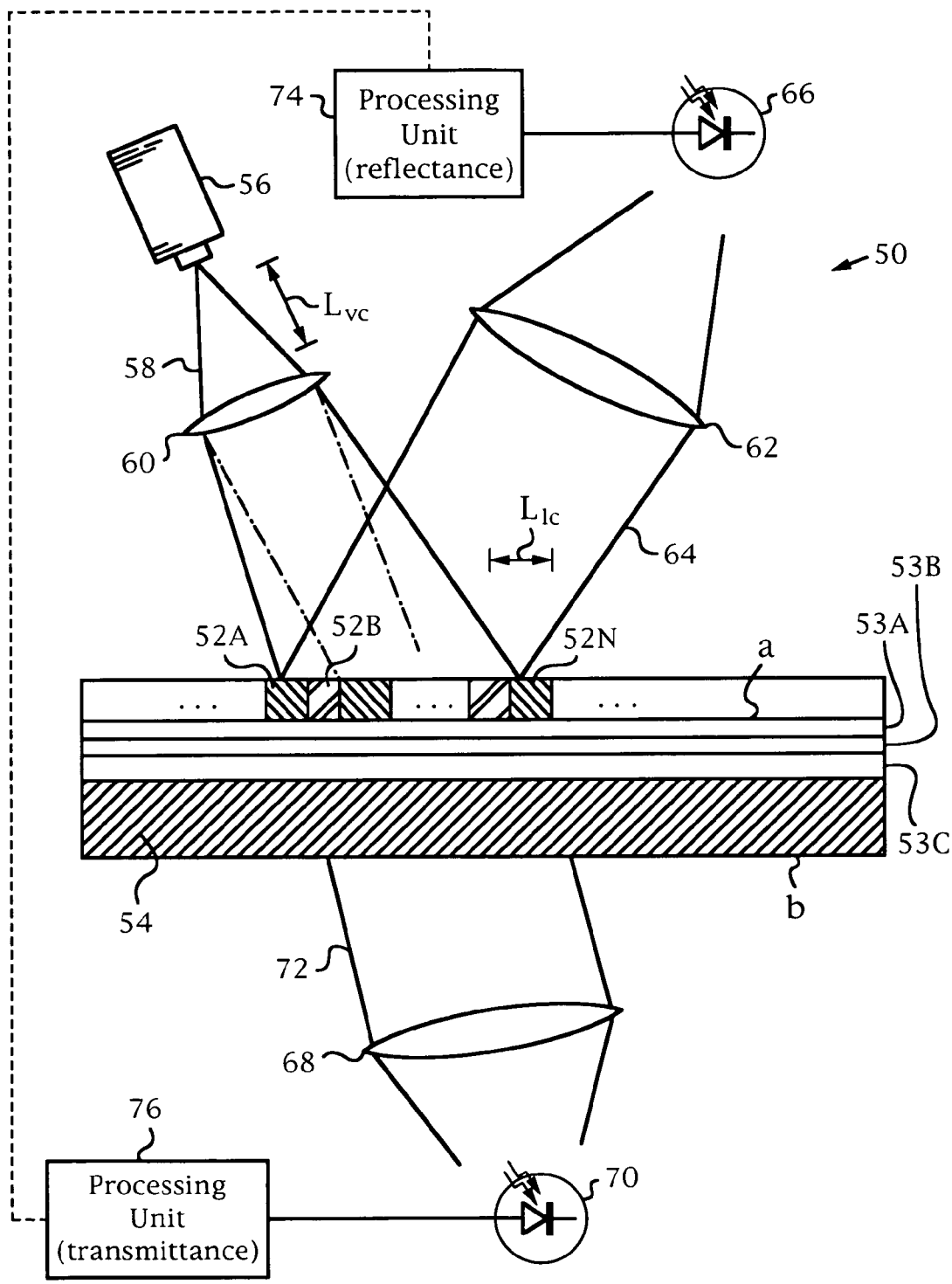
FIG. 2 is a diagram illustrating an apparatus according to the invention for examining a semi-transparent substrate with adjacent features.

The method of invention finds its preferred application in measuring physical properties of features that are adjacent to each other and are located on a semi-transparent or even transparent substrate. FIG. 2 illustrates an apparatus 50 in accordance with the invention for determining one or more physical parameters of features 52A, 52B, . . . 52N on a uniform substrate 54. Features 52A, 52B, . . . 52N are made of two different materials and are positioned adjacent each other. In this embodiment odd numbered features, i.e., 52A, 52C, 52E, . . . etc. are made of material 1 such as amorphous fused silica and even numbered features, i.e., 52B, 52D, 52F, . . . etc. are made of material 2 such as air (air gaps). This type of arrangement of features 52 is encountered, for example, in an Alternating Aperture Phase Shift Mask (AAPSM). It should be understood, that the arrangement of features 52 can be periodic or non-periodic and that features 52 can be made of more than two types of materials.

In addition to adjacent features 52, substrate 54 also carries a number of features in the form of layers 53A, 53B and 53C. Layers 53 can be made of materials different from those of features 52.

Apparatus 50 has an illumination source 56. Illumination source 56 generates an incident light 58 spanning an incident wavelength range $\Delta\lambda$. Preferably source 56 is broadband and its range $\Delta\lambda$ extends from about 190 nm to about 1000 nm. To cover such range source 56 can include a number of individual sources spanning separate or even overlapping portions of wavelength range $\Delta\lambda$. Substrate 54 is at least semi-transparent within wavelength range $\Delta\lambda$. Of course, the actual level of transparency of substrate 54 to incident light 58 may differ greatly between different wavelengths within range Δλ.

Apparatus 50 is equipped with an optic 60 for guiding incident light 58 from source 56 to substrate 54. Optic 60 is shown in the form of a lens, but it is understood that a compound optic system can be used as optic 60. In particular, it is preferred that optic 60 have a beam shaping power such that it can focus or collimate incident light 58 on substrate 54, as indicated in dashed and dotted lines.

An optic 62 is positioned above substrate 54 to guide response light 64 generated in response to incident light 58 by substrate 54 and features 52, 53 to a detector 66. Although optic 62 is shown in the form of a lens, it is understood that a compound optic system can be used as optic 62. Response light 64 is a reflected light and it has a response spectrum corresponding to a reflectance R of substrate 54 and features 52, 53. An additional optic 68 and detector 70 can be provided to also collect a response light 72 transmitted through features 52, 53 and substrate 54. Response light 72 has a response spectrum corresponding to a transmittance T of features 52, 53 and substrate 54.

Apparatus 50 has a detector 66 for receiving response light 64 and a detector 70 for receiving response light 72. Detectors 66, 70 are any suitable photodetectors for receiving response light 64, 72 respectively and measuring a response spectrum of response light 64, 72. More specifically, detectors 66, 70 are designed to measure response light 64, 72 over a response spectrum covering entire wavelength range Δλ.

Furthermore, each detector 64, 70 is connected to a processing unit 74, 76 respectively. Processing units 74, 76 analyze the response spectra and perform computations to obtain computed reflectance and transmittance amplitudes r, t or else import reflectance and transmittance amplitudes r, t from elsewhere. In the embodiment shown units 74, 76 can be in communication with each other, as indicated by the dashed line. It should be noted that in alternative embodiments units 74, 76 can be combined in a single processing device or unit.

During determination of one or more physical parameters of features 52, 53 detectors 66, 70 receive response light 64, 72 from substrate 54 and features 52, 53. Detectors 66, 70 measure the response spectrum of response light 64, 72. In this case detector 66 measures reflectance R and detector 70 measures transmittance T over wavelength range Δλ. Deviations of reflectance R and transmittance T measured by detectors 66, 70 from the values computed using the complex-valued reflectance and transmittance amplitudes r, t are used by processing units 74, 76 to determine the one or more physical parameters of one or more of features 52, 53. The physical parameter or parameters can include a depth or thickness, a width, a real part of the complex refractive index, an imaginary part of the complex refractive index or some other physical parameter of any one of features 52, 53.

Processing units 74, 76 determine the one or more physical properties of features 52, 53 based on a computed complex-valued response for a sample of desired dimensions and material composition and measured response spectrum or spectra, such as the reflectance R and/or transmittance T. In some embodiments the complex-valued response can be computed with the aid of measurements of a suitable reference sample that is built of substrate 54 with features 52, 53 just like the samples to be tested. Alternatively, the complex-valued response can be derived purely mathematically.

During operation, optic 60 guides incident light 58 such that it is incident on an area composing a number of features 52, specifically features 52A through 52N. Since in the present embodiment features 52 may form a periodic structure the area illuminated by incident light 58 should be kept small to avoid possible diffraction effects. Preferably, the area illuminated by incident light 58 should cover a sufficiently small number of features 52 such that diffraction effects are negligible. For example, when working in wavelength range Δλ from 190 nm to 1000 nm with features 52 on the order of tens to hundreds of nanometers, the number of features 52 illuminated by incident light 58 should be kept under 50 and even under 20 in some cases. This condition is not as crucial or may even be unnecessary when features 52 are not arranged in a periodic structure. To take into account the diffraction effects the complex response has to be computed using vector theory. Additional information and relevant teaching on the application of the vector theory can be found in U.S. Pat. Nos. 6,483,580; 5,963,329; 5,739,909 and 5,607,800.

Incident light 58 has a lateral coherence length $L_{lc}$ as indicated. It should be noted that, in general, lateral coherence length $L_{lc}$ is not equal and may differ quite substantially from vertical coherence length $L_{vc}$. When the size of adjacent features 52 is smaller than coherence length $L_{lc}$ the response light 64, 72 from adjacent features 52 is added coherently. Thus, when the area fractions covered by features 52 made of material 1 (i.e., features 52A, 52C, . . . ) and made of material 2 (i.e., features 52B, 52D, . . . ) correspond to $a_1$ and $a_2$, respectively, then the total complex-valued reflectance and transmittance amplitudes are given by the combination of amplitudes of response light 64, 72 from these two areas, as follows:

$$r_C = a_1 r_1 + a_2 r_2, \quad \text{Eq. 9}$$

$$t_C = a_1 t_1 + a_2 t_2, \quad \text{Eq. 10}$$

$$a_1 + a_2 = 1, \quad \text{Eq. 11}$$

where the subscript "C" denotes coherent adding. It should be noted that $r_1$, $r_2$, $t_1$, $t_2$ are the complex-valued reflectance and transmittance amplitudes for areas 1 and 2, respectively, and they may be calculated in accordance with equations 1-2 as discussed above. The response spectra such as a coherent reflectance $R_C$ and a coherent transmittance $T_C$ are computed by multiplying out the complex-valued reflectance and the complex-valued transmittance by their respective complex conjugates as follows:

$$R_C = (a_1 r_1 + a_2 r_2) \cdot (a_1 r_1 + a_2 r_2)^* = a_1^2 R_1 + a_2^2 R_2 + 2 a_1 a_2 \cdot \text{Real}(r_1 r_2^*) \quad \text{Eq. 12}$$

$$T_C = (a_1 t_1 + a_2 t_2) \cdot (a_1 t_1 + a_2 t_2)^* = a_1^2 T_1 + a_2^2 T_2 + 2 a_1 a_2 \cdot \text{Real}(t_1 t_2^*) \quad \text{Eq. 13}$$

where $R_1 = (r_1 \cdot r_1^*)$, $R_2 = (r_2 \cdot r_2^*)$, $T_1 = (t_1 \cdot t_1^*)$, and $T_2 = (t_2 \cdot t_2^*)$ are reflectances and transmittances from areas 1 and 2 respectively.

As discussed above, when substrate 54 is thick, phase $\delta_s$ has to be averaged. $R_1$, $R_2$, $T_1$, and $T_2$ can then be calculated from equations 7 and 8. The cross terms are given by:

$$r_1 \cdot r_2^* \Longrightarrow \langle r_1 \cdot r_2^* \rangle = \frac{1}{2\pi} \int_0^{2\pi} r_1 \cdot r_2^* \, d\delta_s \quad \text{Eq. 14}$$

-continued $$= \frac{r_{1,as}r_{2,as}^* + (t_{1,as}t_{2,as}^*t_{1,sa}t_{2,sa}^* - r_{1,as}r_{2,as}^*r_{2,sa}r_{2,sa}^*)r_{1,sb}r_{2,sb}^*e^{-2\alpha_s d_s}}{1 - r_{1,sa}r_{2,sa}^*r_{1,sb}r_{2,sb}^*e^{-2\alpha_s d_s}}$$

$$t_1 \cdot t_2^* \Rightarrow \langle t_1 \cdot t_2^* \rangle = \frac{1}{2\pi} \int_0^{2\pi} t_1 \cdot t_2^* \, d\delta_s \qquad \text{Eq. 15}$$

$$= \frac{t_{1,as}t_{2,as}^*t_{1,sb}t_{2,sb}^*e^{-\alpha_s d_s}}{1 - r_{1,sa}r_{2,sa}^*r_{1,sb}r_{2,sb}^*e^{-2\alpha_s d_s}} = Ae^{i\phi}$$

In these equations subscripts 1 and 2 represent areas 1 and 2, respectively. A is the amplitude of $\langle t_1 \cdot t_2^* \rangle$ and $\phi$ is the phase difference or shift between $t_1$ and $t_2$. A person skilled in the art will recognize that equation 15 provides a very convenient way for measuring and calculating the phase shift for phase masks such as AAPSMs. Equations 12-15 are novel in providing an analytic and closed form expression for coherent lateral interference between adjacent features on thick transparent or semi-transparent substrates. It should be noted that knowledge of phase shift $\phi$ will be sufficient in some cases to make some determination about physical parameters of features 52, and is a valuable piece of information in and of itself, as will be appreciated by those skilled in the art.

Light 24, 28 have response spectra which are influenced by complex reflectance and transmittance amplitudes $r_C$ and $t_C$. Specifically, the presence of the cross terms $\langle r_1 \cdot r_2^* \rangle$ and $\langle t_1 \cdot t_2^* \rangle$ in equations 12 and 13 affects the response spectra such as the reflectance R and transmittance T over wavelength range $\Delta\lambda$. In fact, because of the cross terms the total reflectance R and total transmittance T within range $\Delta\lambda$ experience interference effects such their sum may be less than 1 (assuming no absorption losses).

Equations 14-15 can be simplified in some cases. For example, when substrate 54 is thick and highly absorbing such that:

$$\alpha_s d_s \gg 1 \text{ or } e^{-\alpha_s d_s} \approx 0,$$

then the expressions for the cross terms can be simplified as follows:

$$\langle r_1 \cdot r_2^* \rangle = r_{1,as}r_{2,as}^*, \text{ and} \qquad \text{Eq. 16}$$

$$\langle t_1 \cdot t_2^* \rangle = 0. \qquad \text{Eq. 17}$$

For measurement purposes, it is sometimes convenient for optic 60 to produce a focused beam of incident light 58 rather than a collimated beam. One extreme case is when the depth of field is much shorter than thickness $d_s$ of substrate 54. If the beam of light 58 is focused on one side of substrate 54, e.g., on side a, then the reflectance from the other side, i.e., side b of substrate 54 will not be detected. Therefore, when the beam of light 58 is focused on side a, which is the front side or front surface, equation 14 will be changed to equation 16 by setting $r_{i,sb}=0$. On the other hand, when the beam of light 58 is focused on side b, which is the back side or back surface, equation 14 will be changed ($r_{i,sa}=0$, $r_{i,as}=0$) to:

$$\langle r_1 \cdot r_2^* \rangle = t_{1,as}t_{2,as}^*t_{1,sa}t_{2,sa}^*r_{1,sb}r_{2,sb}^*e^{-2\alpha_s d_s}. \qquad \text{Eq. 18}$$

$R_1$ and $R_2$ in equation 12 need to be modified accordingly.

When the size of area 1 and 2 is much larger than lateral coherence length $L_{lc}$ of incident light 58, then response light 64, 72 from those two areas add incoherently. Thus, the total reflectance and transmittance are given by:

$$R_I = a_1 R_1 + a_2 R_2, \qquad \text{Eq. 19}$$

$$T_I = a_1 T_1 + a_2 T_2, \qquad \text{Eq. 20}$$

where the subscript "I" denotes incoherent adding. It should be noted that equations 9-10 and 19-20 can be extended to cases where three, four or even more different areas are illuminated.

In most practical embodiments, response light 64, 72 from area 1 and area 2 are partially coherent. Thus, the reflectance R and transmittance T including the contributions of both coherent and incoherent fractions to their response spectra can be described as follows:

$$R = (1-\beta)R_I + \beta R_C, \qquad \text{Eq. 21}$$

$$T = (1-\beta)T_I + \beta T_C, \text{ and} \qquad \text{Eq. 22}$$

$$0 \leq \beta \leq 1 \qquad \text{Eq. 23}$$

where $\beta$ is a fraction for coherent adding. Now, when material 1 and material 2 are identical through the whole stack (i.e., substrate 54 and features 52, 53) then $R = R_I = R_C = R_1 = R_2$ and $T = T_I = T_C = T_1 = T_2$ independent of b, $a_1$ and $a_2$.

Fraction $\beta$, also called the coherence fraction, is related to lateral coherence length $L_{lc}$ as follows:

$$L_{lc} = \frac{\lambda^2}{\Delta\lambda_{spect.}} \qquad \text{Eq. 24}$$

where $\lambda$ is the wavelength and $\Delta\lambda_{spect.}$ is the spectral band width of detectors 66, 70 and preferably covers the entire bandwidth $\Delta\lambda$ of incident light 58. For more information the reader is referred to Grant R. Fowles, *Introduction to Modern Optics*, Second Edition, Dover, 1975, p. 73. Usually, the first order of diffracted response light is used and the grating equation is given by:

$$\lambda = p(\sin\theta_i + \sin\theta_r) \qquad \text{Eq. 25}$$

where p is the period of the grating, and $\theta_i$, $\theta_r$ are the angles for incident and diffracted light. This equation can be re-written as:

$$\Delta\lambda = \sqrt{p^2 - (\lambda - p\sin\theta_i)^2} \, \Delta\theta_r, \qquad \text{Eq. 26}$$

where $\Delta\theta_r$ is the angular spread of the diffracted response light. Using equation 26 coherent fraction $\beta$ can be approximated by:

$$\beta = \frac{\beta_1 \lambda^2}{\beta_0 \sqrt{p^2 - (\lambda - p\sin\theta_i)^2}} \text{ when } \beta < 1, \text{ and} \qquad \text{Eq. 27}$$

$$\beta = 1 \text{ otherwise.}$$

In equation 27 $\beta_1$ is the coherent factor (wavelength independent) and $\beta_o$ is the normalization factor given by:

$$\beta_0 = \frac{\lambda_0^2}{\sqrt{p^2 - (\lambda_0 - p\sin\theta_i)^2}}, \qquad \text{Eq. 28}$$

where $\lambda_o$ is the shortest wavelength in the collected spectrum $\Delta\lambda_i$.

The above equations are used to determine the response spectra, i.e., reflectance R and transmittance T that should be observed by detectors 66, 70 when the sample being measured conforms to the requirements. In practice, processing unit 74 compares these computed or theoretical spectra with actual measured spectra obtained from detectors 66, 70.

It should be noted at this point, that all of the above approaches can be applied to unpolarized light, s-polarized light and p-polarized light. A person skilled in the art will also recognize that the method of invention permits one to perform computations and measurements for a wide variety of feature geometries and materials on semi-transparent and transparent substrates. The below selected examples serve to further illustrate how the method and apparatus of invention are applied for performing measurements on specific samples.

EXAMPLES

Figure 3:
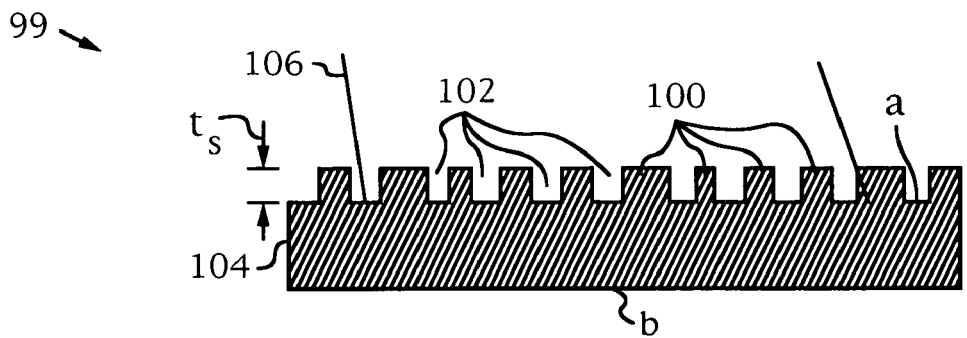
FIG. 3 illustrates a cross-sectional view of a fused silica sample etched with adjacent features.

FIG. 3 illustrates a fused silica sample 99 having adjacent features 100, 102 on a substrate 104. Sample 99 is examined with the aid of apparatus 50 shown in FIG. 2. A beam 106 of incident light 58 spanning wavelength range $\Delta\lambda$ and originating from source 56 is shown. The remainder of apparatus 50 and response light are not shown in FIG. 3 for reasons of clarity. Substrate 104 is made of fused silica and features 100 are mesas of fused silica. Features 102 are trenches or air gaps between mesas 100. Trenches 102 can be etched or produced in accordance with any suitable method known in the art.

In sample 99 material 1 is fused silica and material 2 is air. The area fractions $a_1$ and $a_2$ of mesas 100 and trenches 102 are equal and the depth $t_s$ of trenches 102 is 240.9 nm. The calculated response spectrum of response light (reflected and transmitted light) includes both the reflectance and transmittance spectra R, T obtained by using equations 12 and 13 and plotted in FIG. 4. Reflectance R from front (etched) side a (solid line) and back side b (dashed line) of sample 99 are referenced by 108 and 110 respectively. Transmittance is drawn in solid line indicated by reference number 112. Reflectance 110 from back side b exhibits more oscillations (peaks and valleys). This is because fused silica has a higher refractive index than air. This makes it advantageous to measure reflectance R from the back side b of etched sample 99. This is especially useful when Cr is coated on sample 99, such as when producing an AAPSM mask.

Figure 4:
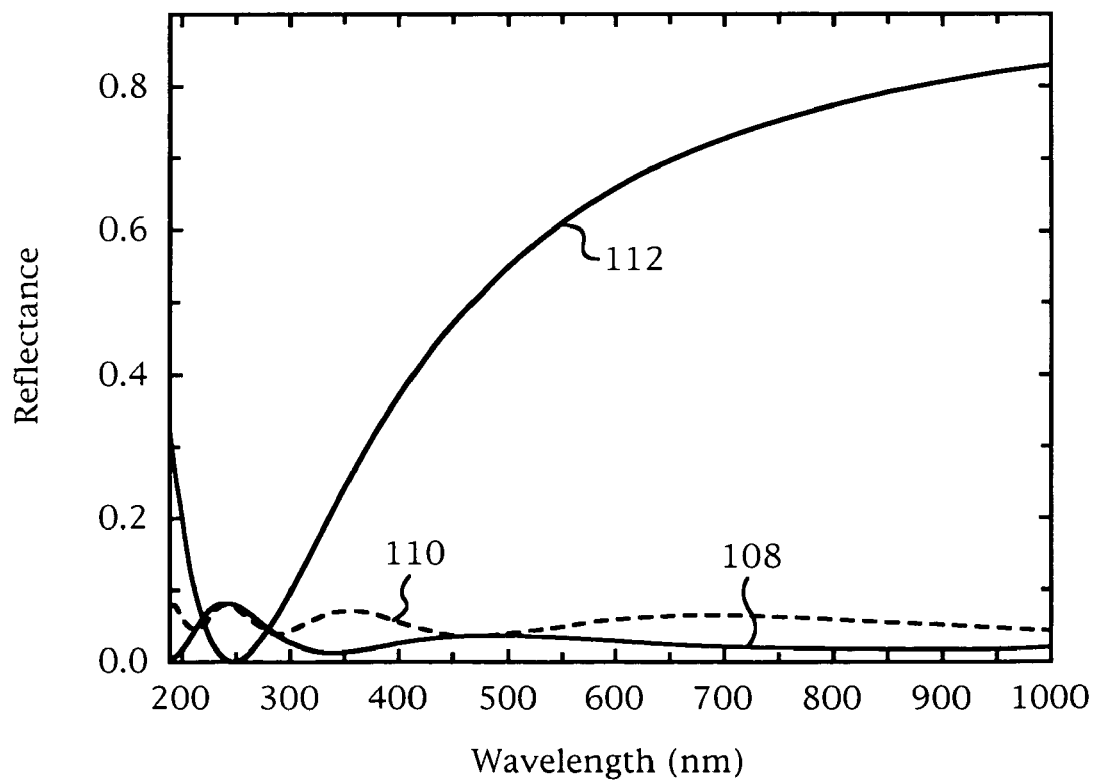
FIG. 4 are graphs of reflectance and transmittance spectra R, T for the sample of FIG. 3.
Figure 5:
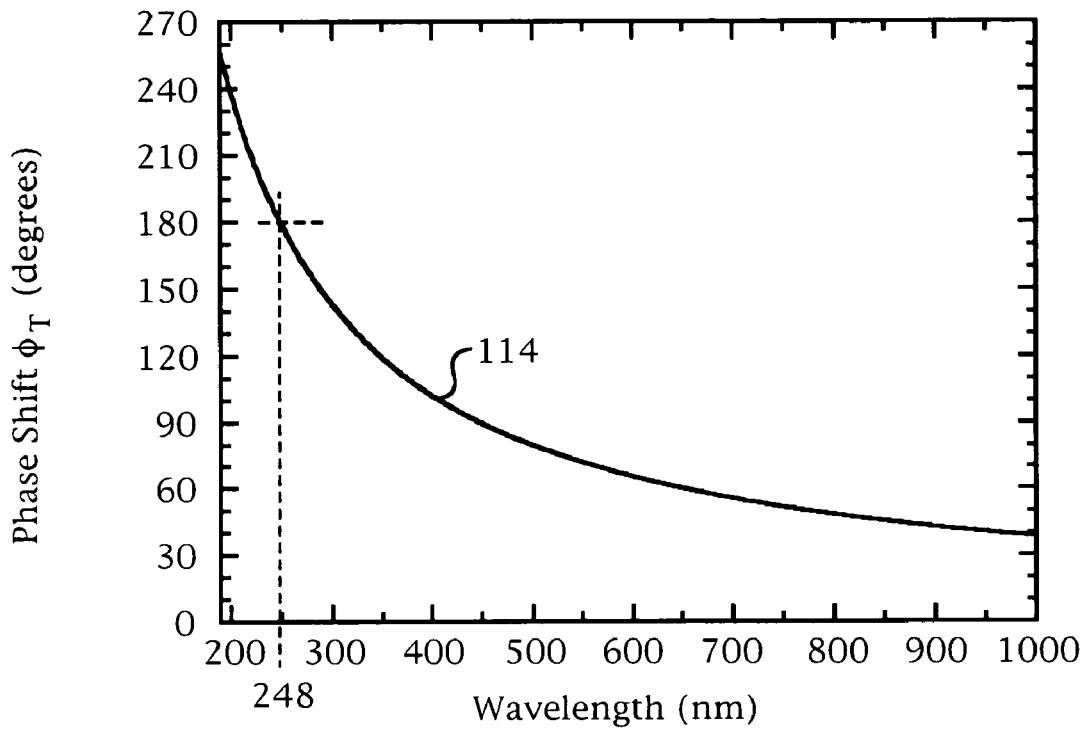
FIG. 5 is a graph of phase shift for the sample of FIG. 3.

The phase $\phi$ is calculated using equation 15, and the results are shown by graph 114 in FIG. 5. The phase shift is 180.0 degrees at a wavelength $\lambda$=248 nm. The destructive interference results in zero intensity in transmittance spectrum 112 at 248 nm as can be seen in FIG. 4, since the area fractions $a_1$ and $a_2$ are 50%.

Figure 6:
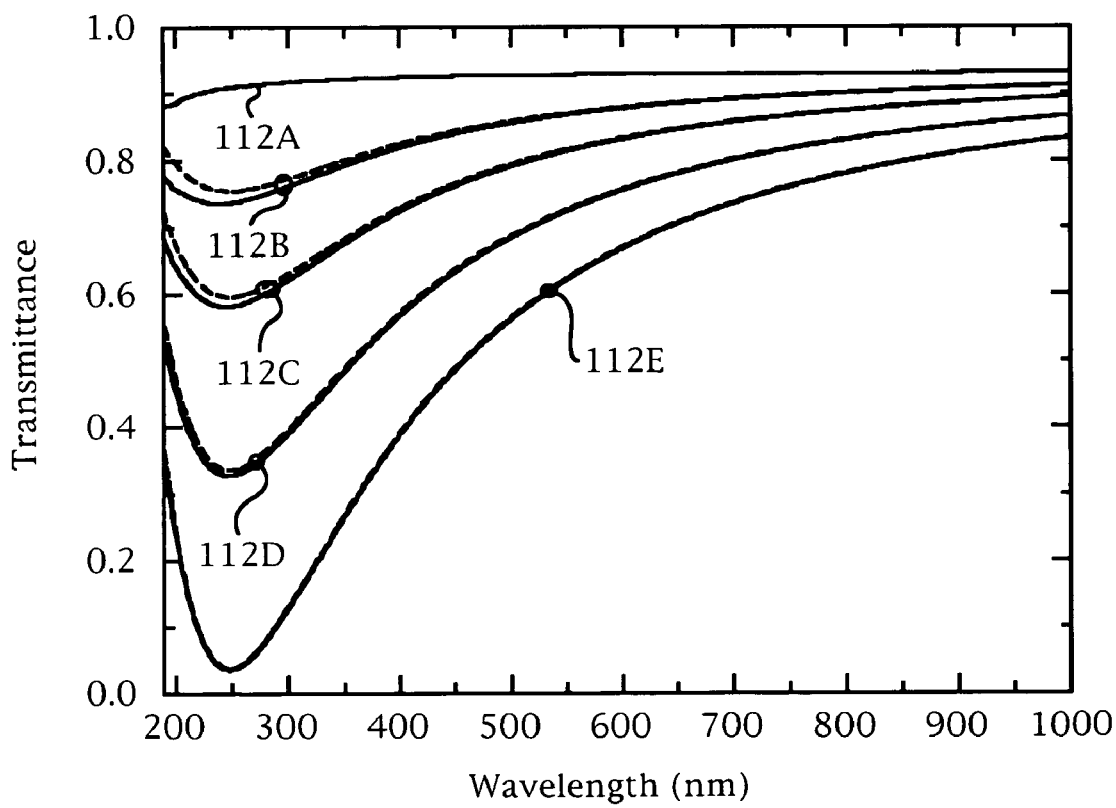
FIG. 6 are graphs of transmittance T spectra for samples analogous to that of FIG. 3 and having varying area fractions of trenches.

The wavelength for the 180 degree phase shift can be directly measured using transmittance spectrum 112, as more clearly shown in FIG. 6. In fact, the solid lines are the raw transmittance spectra 112A, 112B, 112C, 112D and 112E for five different area fractions $a_2$ (0%, 5%, 10%, 20% and 40%) of trenches 102 in samples analogous to sample 99. The positions of the dips are at 248 nm for higher area fractions $a_2$ and slightly off for lower area fractions $a_2$. The dashed lines are the transmittances normalized by the 0% raw transmittance spectrum 112 to remove the wavelength dependence of the substrate 104 spectrum.

With the aid of normalization the dip position is fixed at 248 nm, independent of fractional area $a_2$ covered by trenches 102. This allows one to measure the physical parameter of depth $t_s$ of trenches 102 and phase shift $\phi_T$ at any wavelength $\lambda$ through normalized transmittance (by dividing $T_1$ (=$T_2$) on both sides of equation 13):

$$T_n = a_1^2 + a_2^2 + 2a_1 a_2 \cos\phi_T, \qquad \text{Eq. 29}$$

$$\phi_T = \frac{2\pi(n\cos\theta_2 - \cos\theta_1)t_s}{\lambda}, \qquad \text{Eq. 30}$$

where n is the refractive index of fused silica, $\theta_1$ is the incident angle and angle $\theta_2$ is given by Snell's law (n sin $\theta_2$=sin $\theta_1$ assuming sample 99 is surrounded by air with $n_{air}$=1) and subscript T on phase $\phi$ indicates that the response light is transmitted. In FIG. 6, $\theta_1$=$\theta_2$=0, and $\phi_T$=180° at $\lambda$=248 nm. Using n=1.5148 at 248 nm, in the measurement the measured physical parameter of trench depth of trenches 102 is $t_s$=240.9 nm. This result is in excellent agreement with the actual trench depth (240.9 nm) and illustrates the efficacy and accuracy of the method of invention. Once the trench depth is obtained, the phase shift $\phi_T$ at any wavelength $\lambda$ within range $\Delta\lambda$ can be calculated by using equation 30 and the corresponding value of refractive index n. It should be noted that $T_n$ may have multiple minima when $t_s$ is large.

Similarly, one can obtain the normalized reflectance spectrum $R_1$ on both sides of equation 12:

$$R_n = a_1^2 + a_2^2 + 2a_1 a_2 \cos\phi_R. \qquad \text{Eq. 31}$$

When incident light 58 is illuminated from the back side (side b), $\phi_R$ is simply given by:

$$\phi_R = \frac{4\pi n t_s \cos\theta_2}{\lambda}, \qquad \text{Eq. 32}$$

where the subscript R on phase $\phi$ indicates that the response light is reflected.

Figure 7:
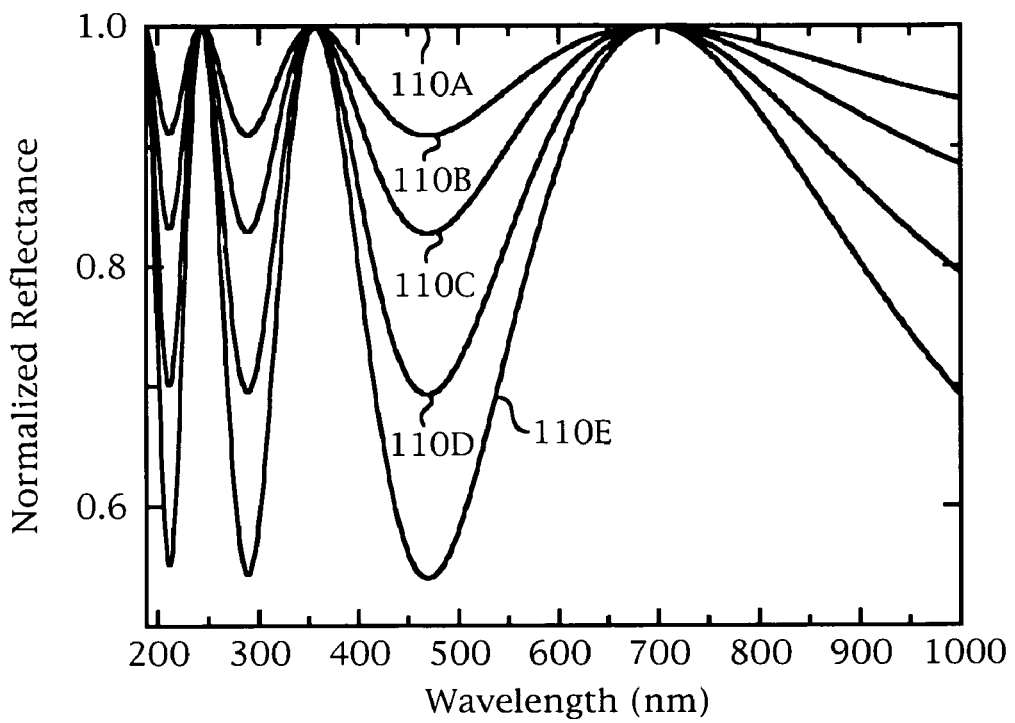
FIG. 7 are graphs of normalized reflectance spectra from back side (b) for samples analogous to that of FIG. 3 and having varying area fractions of trenches.

An example is shown in the graph of FIG. 7 for samples analogous to sample 99 as described above for the same area fractions $a_2$ as studied in FIG. 6 (namely 0%, 5%, 10%, 20% and 40%). The peak and valley positions in the normalized reflectance spectra $R_n$ 110A, 110B, 110C, 110D and 110E taken from back side b remain constant for corresponding area fractions $a_2$ of 0%, 5%, 10%, 20% and 40%. The extremes (peaks and valleys) are found at $\phi_R$=m$\pi$, where m is the interference order and is an even number for peaks and an odd number for valleys. Using equations 31 and 32, one can fit $R_n$ by varying $t_s$ and area fraction $a_2$ with constraints from equation 11. Once $t_s$ is obtained, one can calculate the phase shift for any wavelength $\lambda$ using equation 32. One can also obtain $t_s$ from two data points in the reflectance spectrum $R_n$. For example, one can select two extremes (at $\lambda_1$ and at $\lambda_2$), and calculate $t_s$ as follows:

$$t_s = \frac{\Delta m \lambda_1 \lambda_2}{4|n_1\lambda_2 - n_2\lambda_1|\cos\theta_2},\qquad \text{Eq. 33}$$

where $n_1$ and $n_2$ are the refractive indices of substrate 104 at wavelengths $\lambda_1$ and $\lambda_2$, respectively, and $\Delta m$ is the order difference of the interferences. In FIG. 7 one can choose $\lambda_1=212$ nm (valley) and $\lambda_2=699$ nm (peak), with $n_1=1.539$, $n_2=1.450$, $\Delta m=5$, and $\theta_2=0$. With these parameters equation 33 yields the physical parameter of trench depth of $t_s=241.0$ nm, which is very close to the true value of 240.9 nm. Once again, this attests to the efficacy and accuracy of the method and apparatus of the invention.

When beam 106 of incident light 58 is focused and light 58 is incident from side a, $\phi_R$ for thick substrate 104 is given by:

$$\phi_R = \frac{4\pi t_s \cos\theta_1}{\lambda}.\qquad \text{Eq. 34}$$

Figure 8:
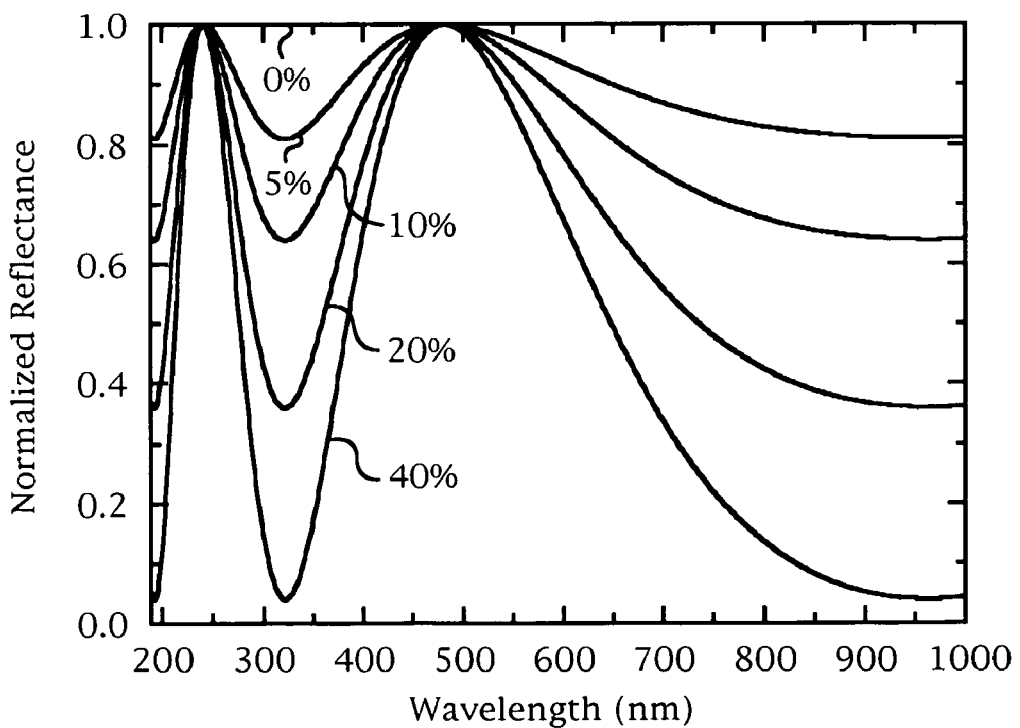
FIG. 8 are graphs of normalized reflectance spectra from front side (a) for samples analogous to that of FIG. 3, normalized relative to a uniform sample, and having varying area fractions of trenches.

In this case phase $\phi_R$ is independent of the refractive index. Hence, one can fit equations 31 and 34 by simply adjusting $a_1^2$, $a_2^2$ and $t_s$. One can also use equation 33 to calculate $t_s$, with $n_1=n_2=1.0$. Graphs of normalized reflectances for incident light 58 being illuminated from side a and area fractions $a_2$ ranging from 0% to 40% as above are shown in FIG. 8. Note that incident light 58 is focused on front side a in this case.

Figure 9:
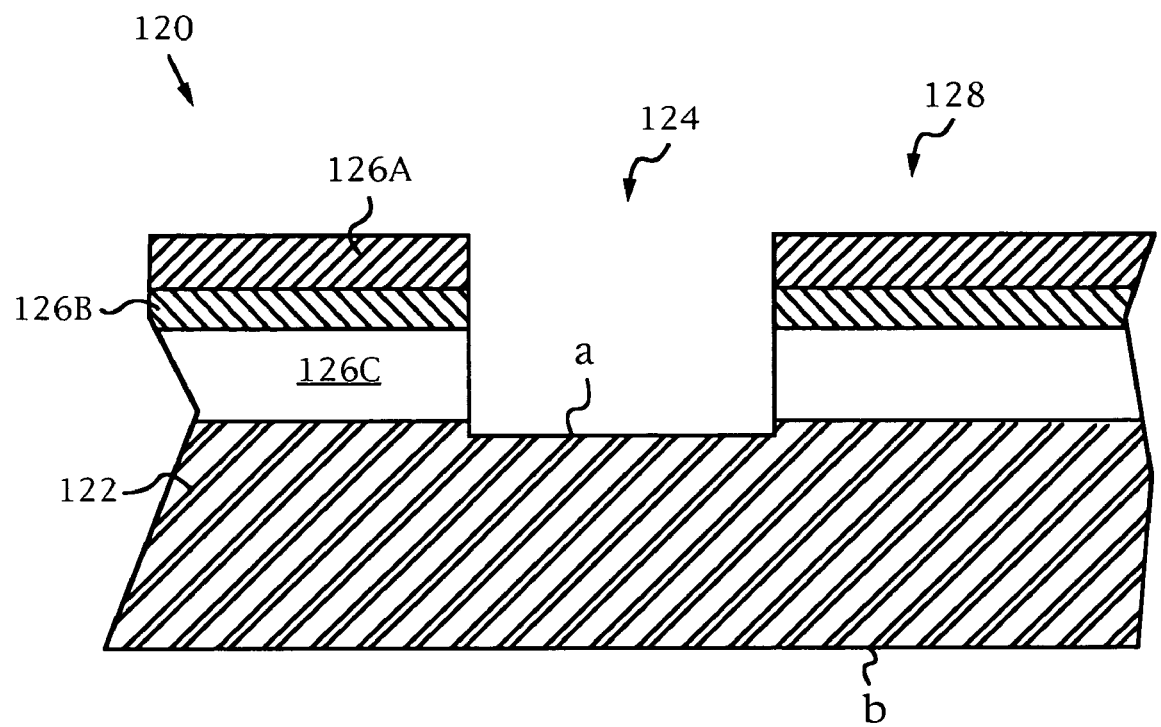
FIG. 9 is a cross sectional view of a portion of another fused silica sample examined with the method of the invention.
Figure 10:
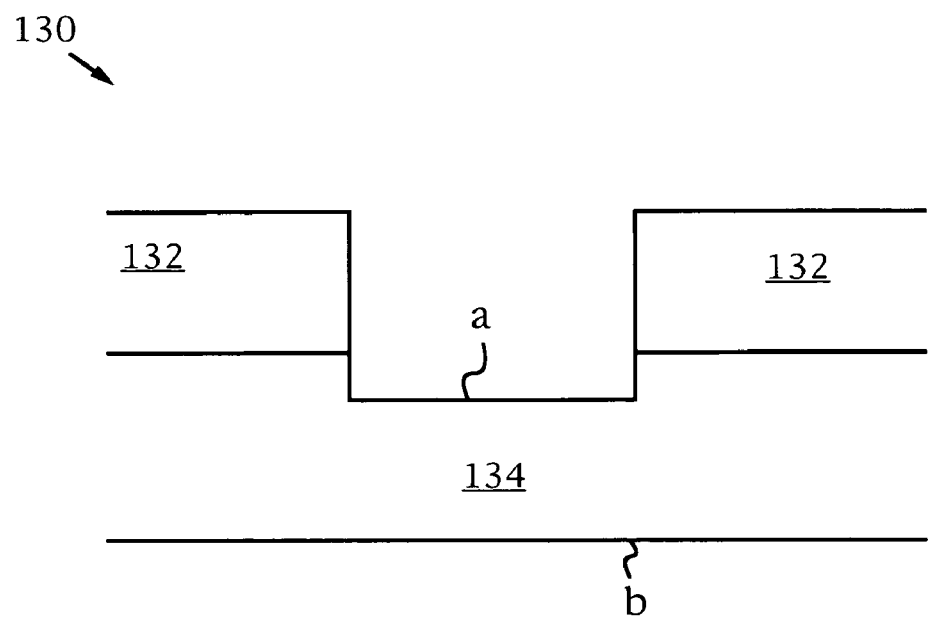
FIG. 10 is a cross sectional view of a portion of yet another fused silica sample examined with the method of the invention.

FIG. 9 shows a portion of another sample 120 having a substrate 122 of fused silica with trenches 124 (only one shown in FIG. 9). In sample 120 substrate 122 has three films 126A, 126B and 126C on side a. Features 128 are mesas between trenches 124 passing down through all three films 126A, 126B and 126C. The depth of trenches 124 can be measured from front side a or from is back side b using equations 21 and 22. In general, the measurement from back side b is more sensitive to substrate 122 recess. This is particularly true for samples in which there is a metal film. For example, a sample 130 with a layer 132 of Cr on side a of a fused silica substrate 134 as shown in FIG. 10 is best examined from back side b.

Figure 11:
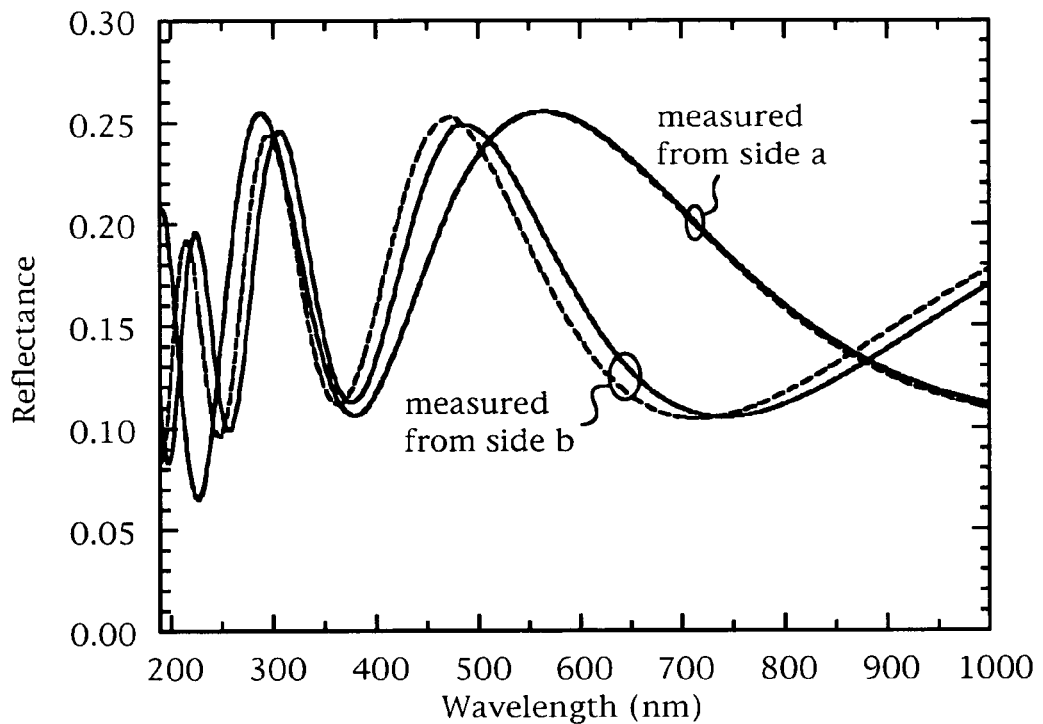
FIG. 11 are graphs of reflectance R spectra measured on the sample of FIG. 10 from the front side and the back side.

FIG. 11 illustrates the graphs for reflectance measurements on sample 130 from front side a and from back side b. The thickness of layer 132 of Cr and recess in fused silica were held constant at a total value of 300.9 nm. The recess itself was tested at two values: 240.9 nm (solid line) and 230.9 nm (dashed line), respectively. The measurement from front side a shows no sensitivity to the change of recess whereas the measurement from back side b shows great sensitivity.

Alternative Embodiments

Figure 12:
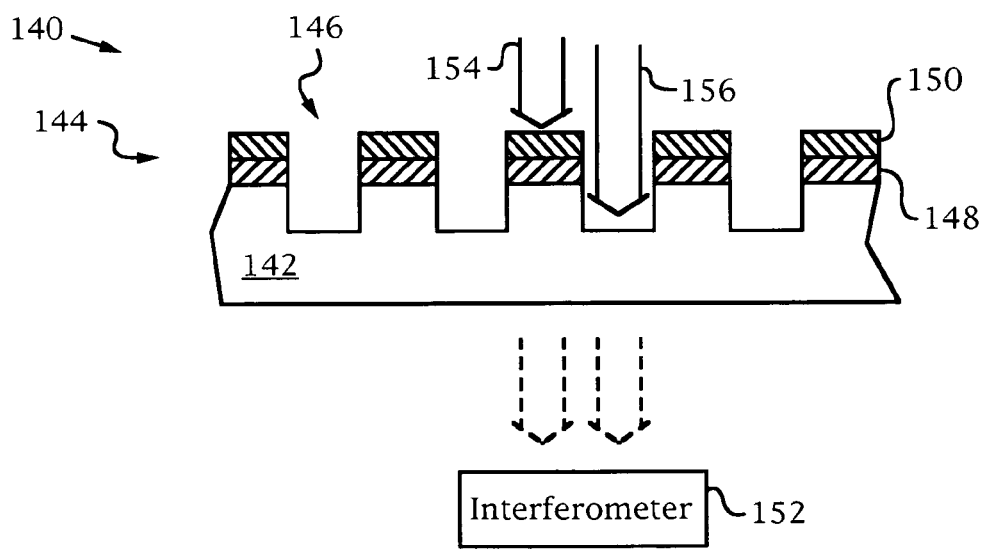
FIG. 12 (PRIOR ART) is a diagram of a standard transmission-type interferometric apparatus examining a substrate with features.

The present method and apparatus are superior to prior art solutions, such as the standard transmission-type interferometric apparatus 140 shown in FIG. 12 for comparison purposes. Specifically, apparatus 140 is not convenient for examining a substrate 142 with features that include mesas 144 and air gaps 146. In this case mesas have three layers including at the bottom a layer of the substrate material, on top of which are located layers 148 and 150. An interferometer 152 is positioned to receive two beams 154, 156 passing through two adjacent features 144, 146.

The limitations of interferometric apparatus 140 are, among other, the fact that beams 154, 156 have to be transmitted through substrate 140 and features 144, 146 in order to enable measurement of physical parameters of features 144, 146. When one of layers 148, 150 or substrate 142 are not transparent, then apparatus 140 will not be able to perform the measurement.

Figure 13:
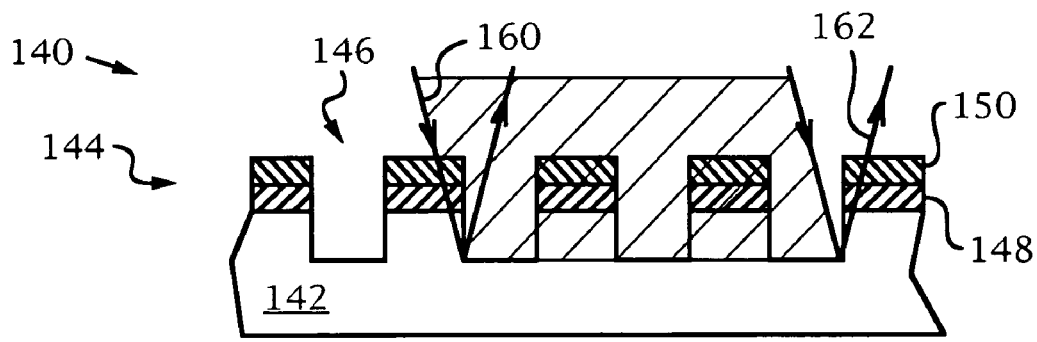
FIG. 13 is a diagram illustrating the method of invention using response light reflected from the front side of the substrate with features as shown in FIG. 12.
Figure 14:
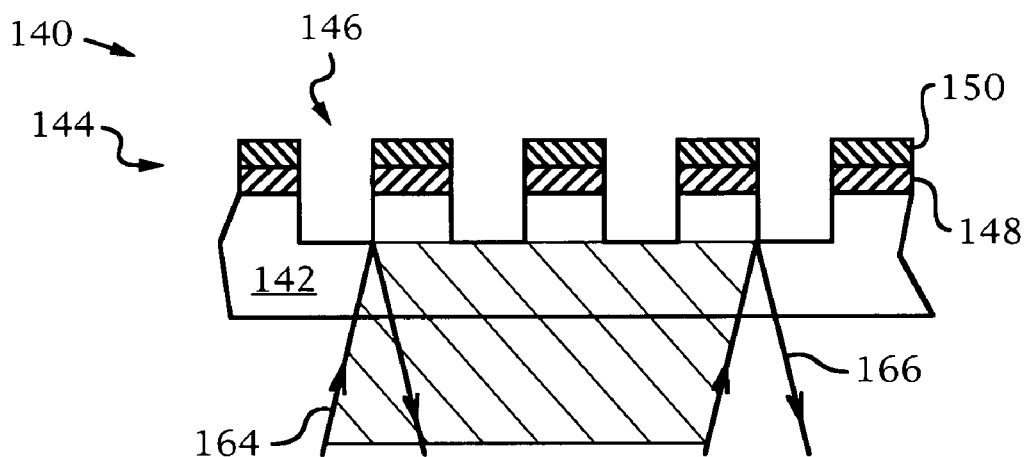
FIG. 14 is a diagram illustrating the method of invention using response light reflected from the back side of the substrate with features as shown in FIG. 12.
Figure 15:
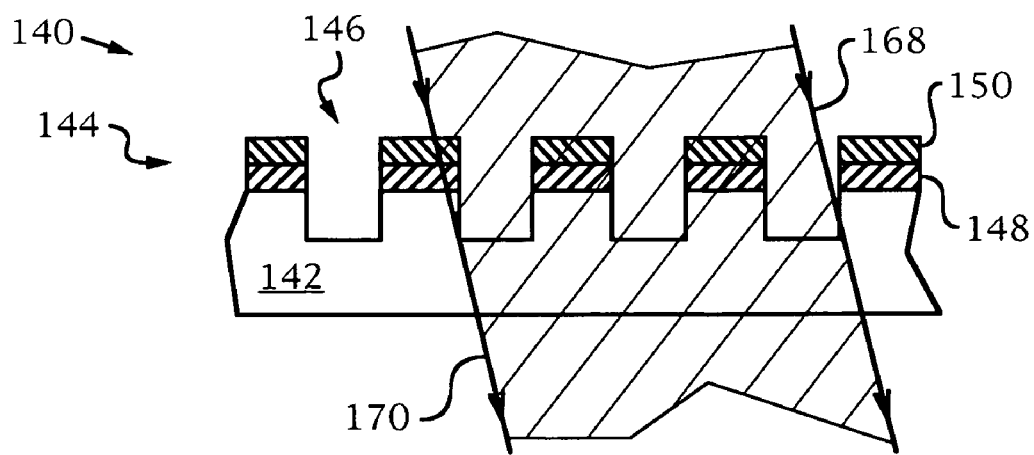
FIG. 15 is a diagram illustrating the method of invention using transmitted response light from substrate with features as shown in FIG. 12.

In contrast, an apparatus according to the present invention offers a number of options for measuring one or more physical parameters of features 144, 146 on substrate 142 irrespective of the transmissibility of layers 148, 150. As shown in FIG. 13 this can be performed in the reflective mode using a beam of incident light 160 and a reflected response light 162. Alternatively, a beam of incident light 164 illuminates substrate 142 from the back side to produce a reflected response light 166, as shown in FIG. 14. As noted in the examples above, under certain circumstances measurement using reflected response light 166 from the back side will provide higher accuracy measurements than light 162 reflected from the front side. In still another embodiment, a beam of incident light 168 is directed at substrate 142 and a transmitted response light 170 is measured. As will be appreciated by a person skilled in the art, a combination of all three methods illustrated in FIGS. 13-15 can be used depending on the transmission and reflection properties of substrate 142 and features 144, 146.

Figure 16:
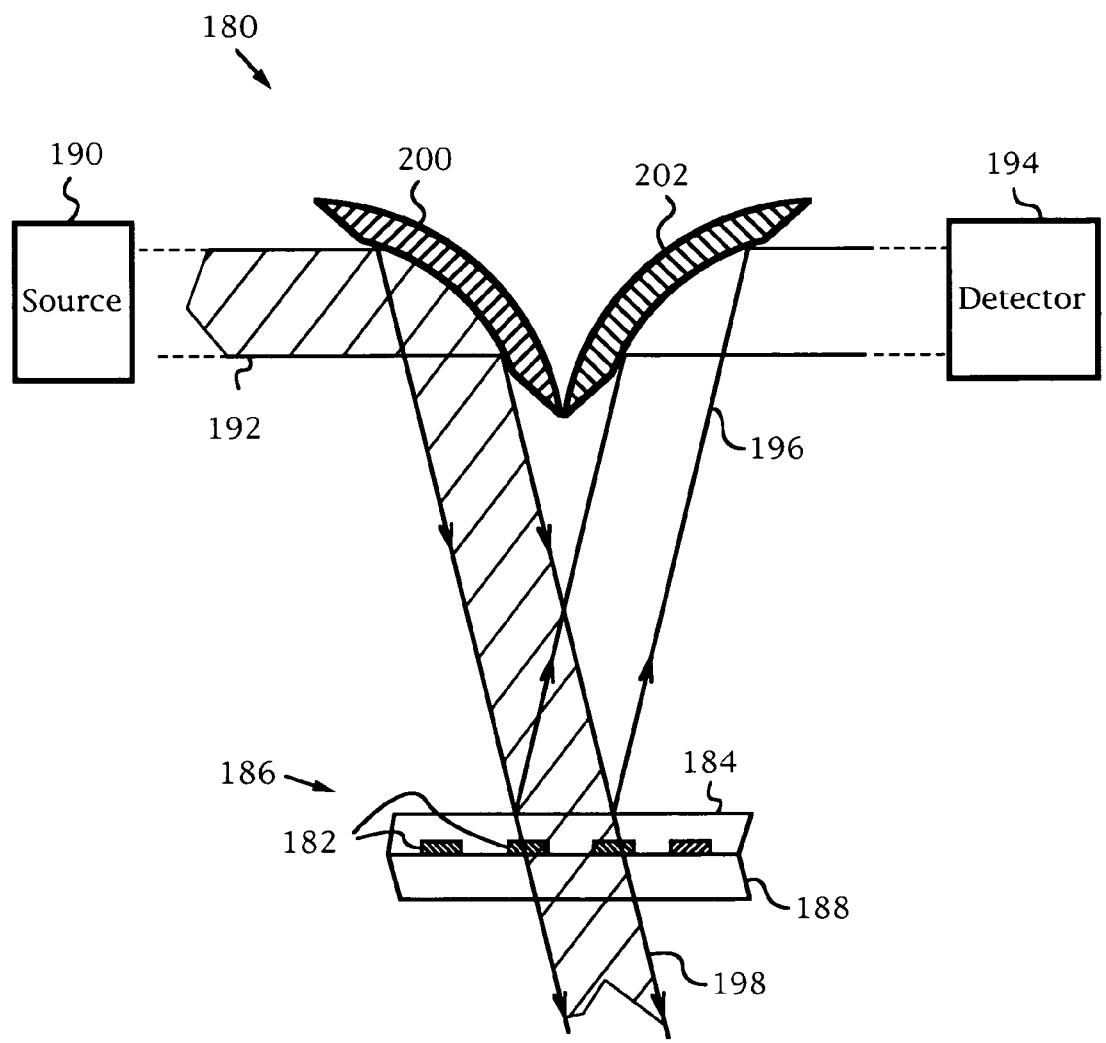
FIG. 16 illustrates a portion of another apparatus according to the invention.

FIG. 16 illustrates a portion of yet another apparatus 180 for examining physical parameters of features 182, 184 of a sample 186. In this embodiment features 182 are embedded within feature 184. Feature 184 is a flat film deposited on a semi-transparent substrate 188. Apparatus 180 has a source 190 for producing a beam of incident light 192 for illuminating sample 186. Apparatus 180 has a detector 194 for examining a response light 196 reflected by sample 186. It should be noted that a transmitted response light 198 can also be measured as necessary. Transmitted response light 198 can be measured by detector 194 with the aid of additional optics (not shown) or a separate detector and optics (not shown).

Apparatus 180 takes advantage of the fact that refractive, catadioptric or purely reflective optics can be used to guide incident light 192 and response light 196 (198). In fact, purely reflective optics are advantageous when incident wavelength range $\Delta\lambda$ is large, e.g., when it extends from 190 nm to 1000 nm. In the present embodiment $\Delta\lambda$ is large and thus apparatus 180 employs a set of reflective optics 200, 202 in the form of curved mirrors. Mirror 200 directs incident light 192 to sample 186. Mirror 202 receives response light 196 from sample 186 and directs it to detector 194. In a preferred version of apparatus 180 mirrors 200, 202 are toroidal mirrors. For general information about the use of toroidal mirrors the reader is referred to U.S. Pat. No. 5,991,022.

Direct Phase Measurement

A further aspect of the present invention is providing an approximate direct measurement of feature phase shift using transmitted light. The result of Eq. 13 can be expressed as $$T_C = a_1^2 T_1 + a_2^2 T_2 + 2a_1 a_2 \cdot |C| \cdot \sqrt{T_1 T_2} \cos(\phi)\qquad \text{Eq. 35}$$

where the complex correction factor C is given by $$C = \frac{\sqrt{[1-|r_{1,sa}^2 \cdot r_{1,sb}^2|\exp(-2\alpha d)] \cdot [1-|r_{2,sa}^2 \cdot r_{2,sb}^2|\exp(-2\alpha d)]}}{1 - r_{1,sa} \cdot r_{2,sa}^* \cdot r_{1,sb} \cdot r_{2,sb}^* \cdot \exp(-2\alpha d)}. \quad \text{Eq. 36}$$

Figure 17:
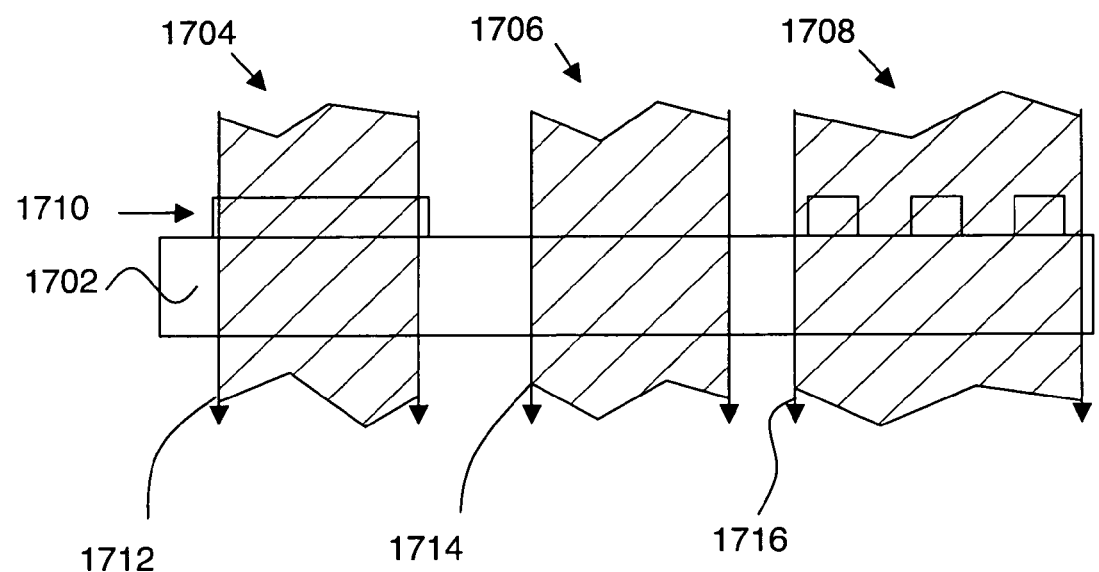
FIG. 17 shows transmission characterization according to an embodiment of the invention.

FIG. 17 shows a typical experimental situation where the result of Eq. 35 is applicable. Features 1710 are disposed on a substrate 1702. Light 1712 is transmitted through first part 1704 of features 1710 and has a measured transmittance $T_1$. Light 1714 is transmitted through a second part 1706 of features 1710 and has a measured transmittance $T_2$. Light 1716 is transmitted through a third part 1708 of features 1710 and has a measured transmittance $T_C$. A fraction $a_1$ of the third part 1708 is similar to first part 1704 and a fraction $a_2$ of the third part 1708 is similar to second part 1706. Thus, in the example of FIG. 17, $a_1$ is the line fraction of part 1708 and $a_2$ is the space fraction of part 1708.

Eq. 35 can be used to express the phase difference between line and space features in terms of the area fractions, measured transmittance spectra, and the complex correction factor as given by $$\cos(\phi) = \frac{T_C - a_1^2 T_1 - a_2^2 T_2}{2a_1 a_2 |C| \sqrt{T_1 T_2}}, \quad \text{Eq. 37a}$$

or as given by $$|C|\cos(\phi) = \frac{T_C - a_1^2 T_1 - a_2^2 T_2}{2a_1 a_2 \sqrt{T_1 T_2}}. \quad \text{Eq. 37b}$$

In many cases of practical interest, it turns out that $C \approx 1$. For example, the backside reflectances $r_{1,sb}$ and $r_{2,sb}$ can be neglected (i.e., set to zero) in cases where the beam is focused on the front surface of the sample being characterized and the substrate is thick relative to the beam depth of focus. Since $T_1$, $T_2$ and $T_C$ are directly measured quantities, and $a_1$ and $a_2$ are accurately known from the mask (or sample) design, assuming $C \approx 1$ leads to the following approximate result for the phase:

$$\cos(\phi) = \frac{T_C - a_1^2 T_1 - a_2^2 T_2}{2a_1 a_2 \sqrt{T_1 T_2}}. \quad \text{Eq. 38}$$

A noteworthy feature of the phase estimate of Eq. 38 is that it is obtained directly (i.e., without any need for modeling or curve fitting). Such directness is a significant advantage in practice, since modeling or curve fitting often introduces uncertainties in the final results.

In some cases, such as characterization of a phase shift mask, the phase is the primary quantity of interest. The phase can also be related to other quantities of interest. The approximation of Eq. 38 (i.e., neglect of multiple reflections) is consistent with the following relation between the phase $\phi$ and the transmission coefficients $t_{uv}$:

$$\phi = arg(t_{1,as}) + arg(t_{1,sb}) - arg(t_{2,as}) - arg(t_{2,sb}). \quad \text{Eq. 39a}$$

To the first order approximation (i.e., ignoring multiple reflections at each interface), the phase difference can be approximated by the optical path difference $$\phi = \sum_i 2\pi t_i (n_{1,i} - n_{2,i})/\lambda. \quad \text{Eq. 39b}$$

Here $n_{1,i}$ and $n_{2,i}$ are the real parts of the complex indices for layer i of areas (or parts) 1 and 2 respectively. The phase has a linear dependence on layer thickness $t_i$. Thus the phase estimate of Eq. 38 can be used to provide a thickness estimate with Eq. 39b.

Figure 18:
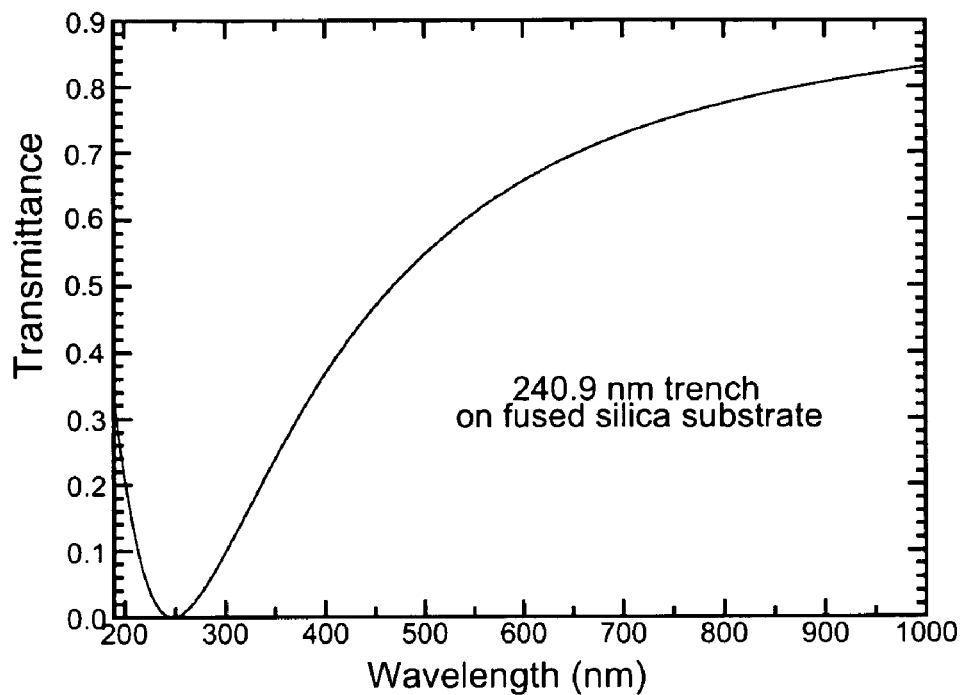
FIG. 18 shows transmittance vs. wavelength for a 240.9 nm deep trench on a fused silica substrate.
Figure 19A:
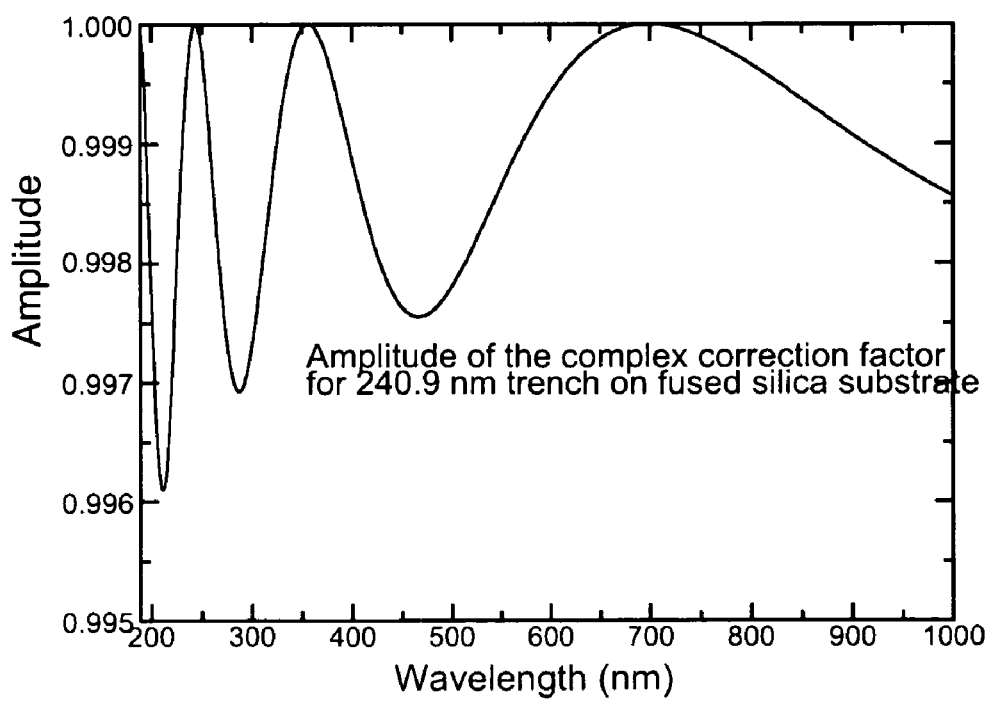
FIGS. 19a-b show amplitude and phase of the complex correction factor vs. wavelength for the example of FIG. 18.
Figure 19B:
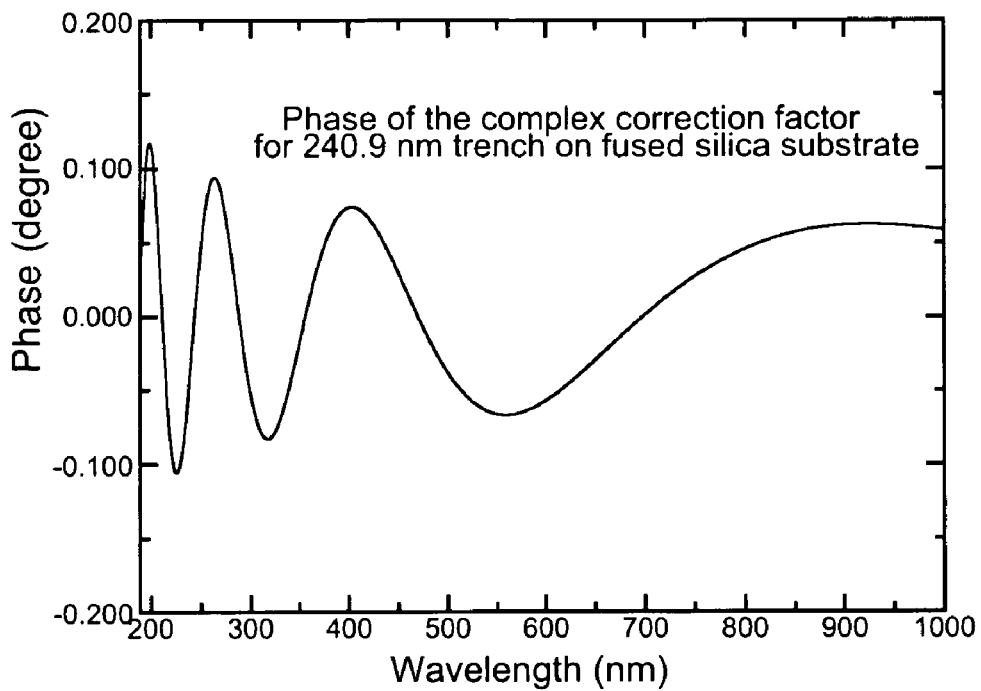
Figure 20A:
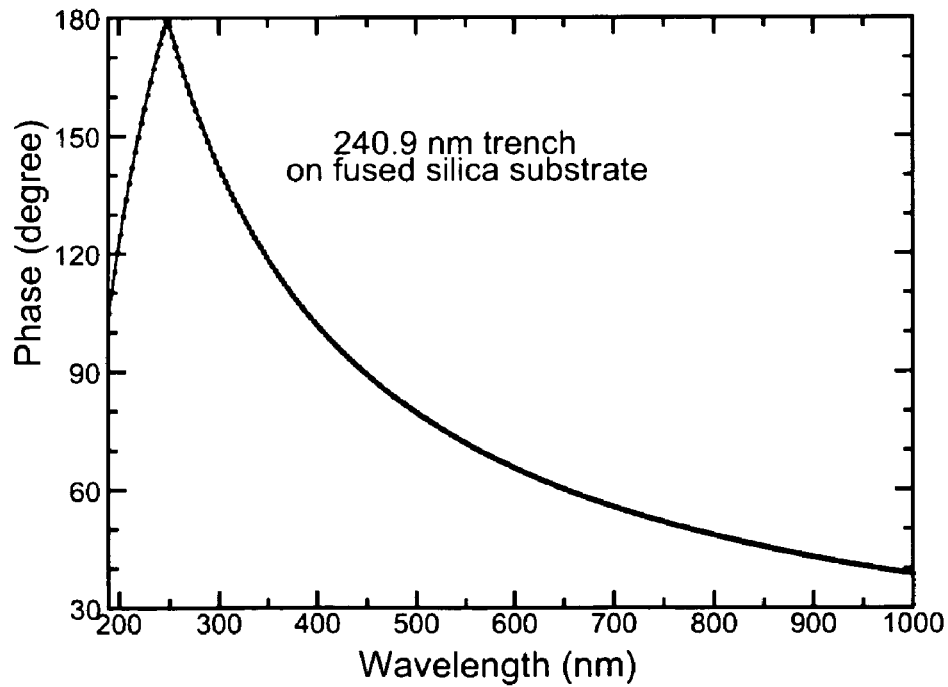
FIGS. 20a-c show direct phase estimates compared to the exact phase over various wavelength ranges for the example of FIG. 18.
Figure 20B:
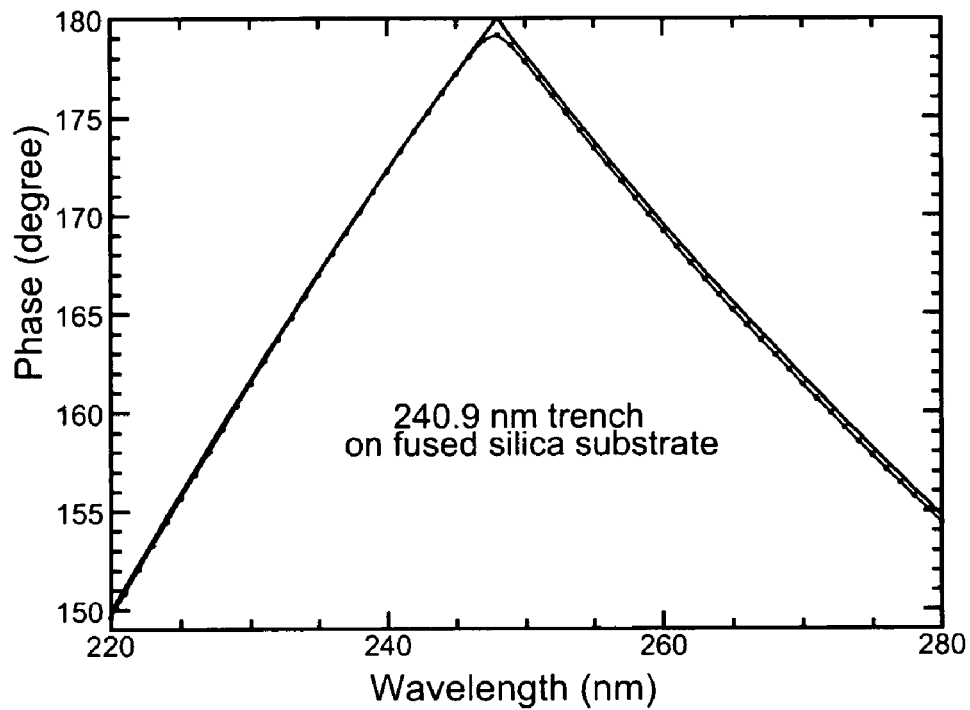
Figure 20C:
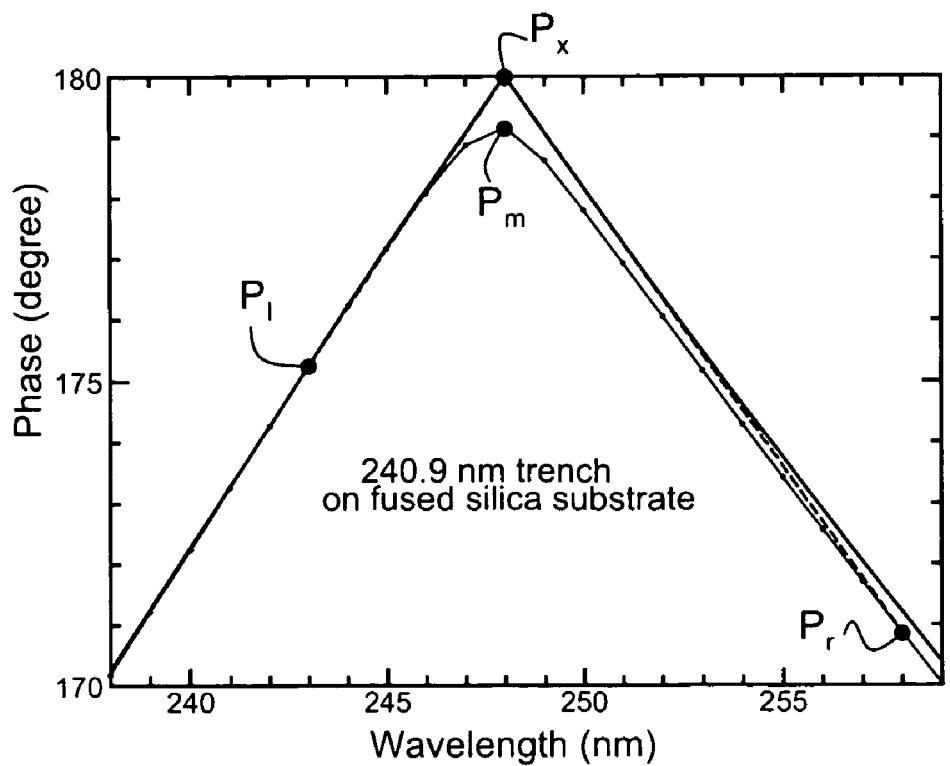

FIG. 18 shows transmittance vs. wavelength for a quartz substrate (thickness of 6.38 mm) having etched trenches (i.e., spaces) with a depth of 240.9 nm. The space to line ratio is 1:1. For this first example, the amplitude and phase of the complex correction factor C are plotted on FIGS. 19a and 19b respectively. In this case, the assumption of Eq. 38 (i.e., that $C \approx 1$) is well satisfied, since the amplitude of C varies from 0.996 to 1, and the magnitude of the phase of C is less than 0.13 degree. FIGS. 20a-c show the approximate phase calculated according to Eq. 38 (line with dots) compared to the exact phase (solid line). The two curves are indistinguishable on FIG. 20a. FIGS. 20b-c show that the difference between exact and approximate phase is largest near the 180 degree point of the exact curve.

The maximum difference between exact and approximate phase is about 0.8 degree. In some cases, this will be a sufficiently accurate approximation. However, it is possible to improve the approximation with a correction. As shown on FIG. 20c, left and right points ($P_l$ and $P_r$) are selected on the approximate curve on opposite sides of the maximum phase point ($P_m$). The points $P_l$, $P_m$ and $P_r$ have corresponding wavelengths $\lambda_l$, $\lambda_m$, and $\lambda_r$ respectively. An intermediate point ($P_x$) having a phase of 180 degrees and a wavelength of $\lambda_m$ is defined. For wavelengths between $\lambda_l$ and $\lambda_m$, the correction entails interpolating between $P_l$ and $P_x$. For wavelengths between $\lambda_m$ and $\lambda_r$, the correction entails interpolating between $P_x$ and $P_r$. In the example of FIG. 20c, $P_l$ is at $\lambda_l$=243 nm (5 nm to the left of the peak), $P_m$ is at $\lambda_m$=248 nm (at the peak), and $P_r$ is at $\lambda_r$=258 nm (10 nm to the right of the peak). Linear interpolation between points $P_l$ and $P_x$ and $P_x$ and $P_r$ is shown with dashed lines. With this correction, the maximum phase error is reduced to about 0.1 degree. This correction is based on two observations. The first is that the exact and approximate phase peaks on FIG. 20c have the same wavelength. The second observation is that the phase should reach exactly 180 degrees as the wavelength varies, since phase is typically a monotonic function of wavelength. Note that the restriction of phase to lie between 0 and 180 degrees on FIGS. 20a-c results from the definition of the inverse cosine function. The above correction is motivated by these two observations.

Figure 21:
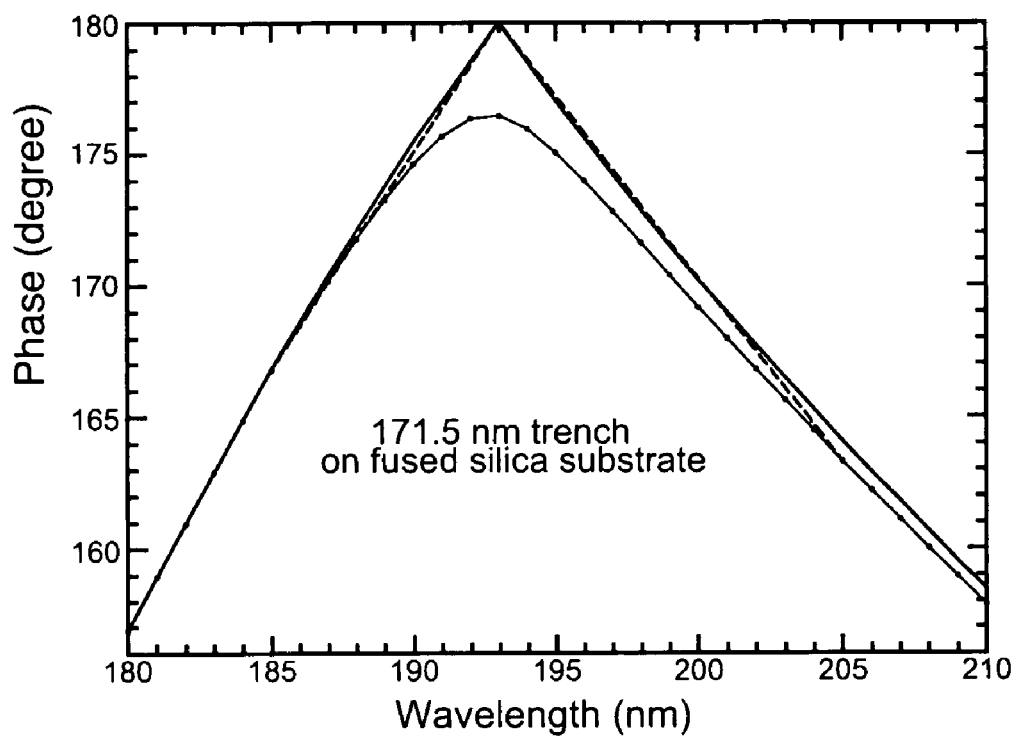
FIG. 21 shows direct phase estimates compared to the exact phase vs. wavelength for a 171.5 nm deep trench on a fused silica substrate.

FIG. 21 shows a plot similar to that of FIG. 20c for a second example having 171.5 nm deep trenches (i.e. spaces) on a fused silica substrate with a 1:1 line to space ratio. As before the solid line is the exact phase, the line with dots is the phase estimate from Eq. 38, and the dashed lines show the interpolation correction. Here $P_l$ is at $\lambda_l$=185 nm, $P_m$ is at $\lambda_m$=193 nm (at the peak), and $P_r$ is at $\lambda_r$=205 nm. Again, the interpolation correction provides a significant improvement in accuracy. Since phase shift masks are often designed to operate at the 180 degree point, this correction is especially valuable for direct characterization of phase shift masks.

Direct phase measurement according to the invention is also helpful in characterizing thin features. A problem which arises when characterizing thin features is that the resulting transmission spectrum has fewer well-defined features (especially maxima and minima) than a spectrum from a thick feature. This problem can be alleviated by direct phase measurements. The basic idea is to employ a first sample having a thick reference feature to aid characterization of a second sample having a thin feature. The thick and thin features are made of the same material and therefore have the same refractive index (as a function of wavelength).

Figure 22:
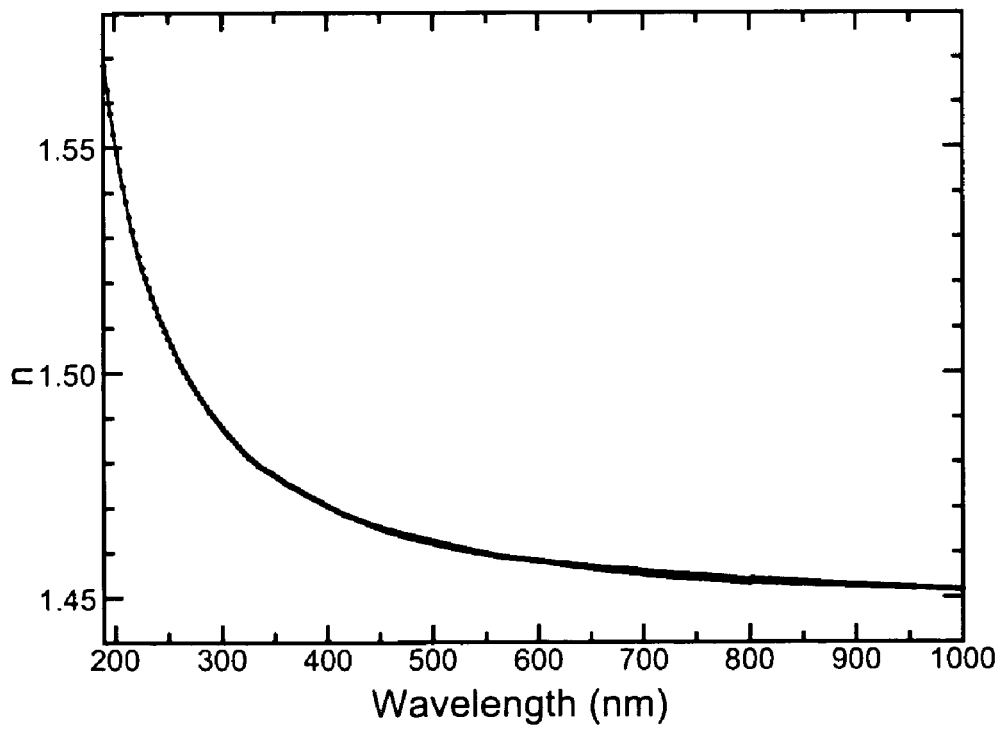
FIG. 22 shows a comparison of two n(λ) plots obtained from different trench depths.

For features having a single patterned layer defined by etching, we have $n_2=1.0$ (the index of air) and $n_1$ is the index of the patterned material. In this case, Eq. 39b can be simplified and rearranged to give $$n_1 = \frac{\phi \lambda}{2\pi t} + 1 \qquad \text{Eq. 40}$$

where t is the feature thickness. Thus if the thickness t is known (e.g., from an independent measurement), the direct measurement of phase according to Eq. 38 provides a simple direct measurement of $n_1(\lambda)$. The consistency of this approach is demonstrated on FIG. 22, where the solid line is calculated for t=200 nm, and the line with dots is calculated for t=300 nm. The two curves are nearly indistinguishable, especially for wavelengths less than 600 nm. Thus characterization of a thick reference sample according to Eqs. 38 and 40 gives $n_1(\lambda)$. The thickness of a thin feature having the same index $n_1(\lambda)$ can then be determined by fitting Eq. 40 to directly measured (i.e., from Eq. 38) phase data using the thin feature thickness t as a fitting parameter. This fit is a linear least squares fit, which can be computed rapidly compared to the nonlinear fit typically required in conventional approaches which do not make use of direct phase measurements. Once the thickness t of the thin feature is known, the phase can be calculated from t and $n_1(\lambda)$ using Eq. 40. This computation of phase from t can be useful in cases where it is desirable to find the 180 degree point of the thin feature from phase measurements on the thin feature which do not include the phase peak.

Figure 23:
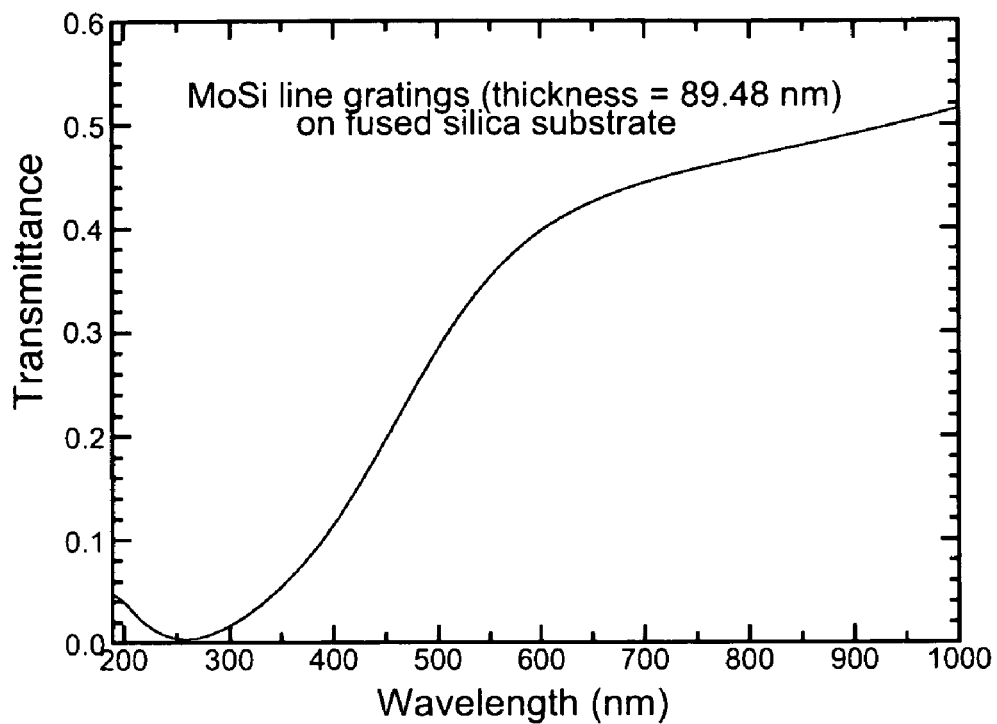
FIG. 23 shows transmittance vs. wavelength for a 89.48 nm deep MoSi line on a fused silica substrate.

FIG. 23 shows transmittance vs. wavelength for a third example, having MoSi lines on a fused silica substrate where the line to space ratio is 3:1. The thickness of the MoSi lines is 89.48 nm. With this sample configuration, the measured transmittance is close to zero at the wavelength of interest when the phase shift is 180 degrees, which gives the best interference contrast. More specifically, $a_1^2 T_1 + a_2^2 T_2$ is about equal to $$2a_1 a_2 \sqrt{T_1 T_2}$$

at 248 nm for this case. Design of such preferred characterization samples can be guided by experiment and/or by modeling, and can be done by one of ordinary skill in the art.

Figure 24:
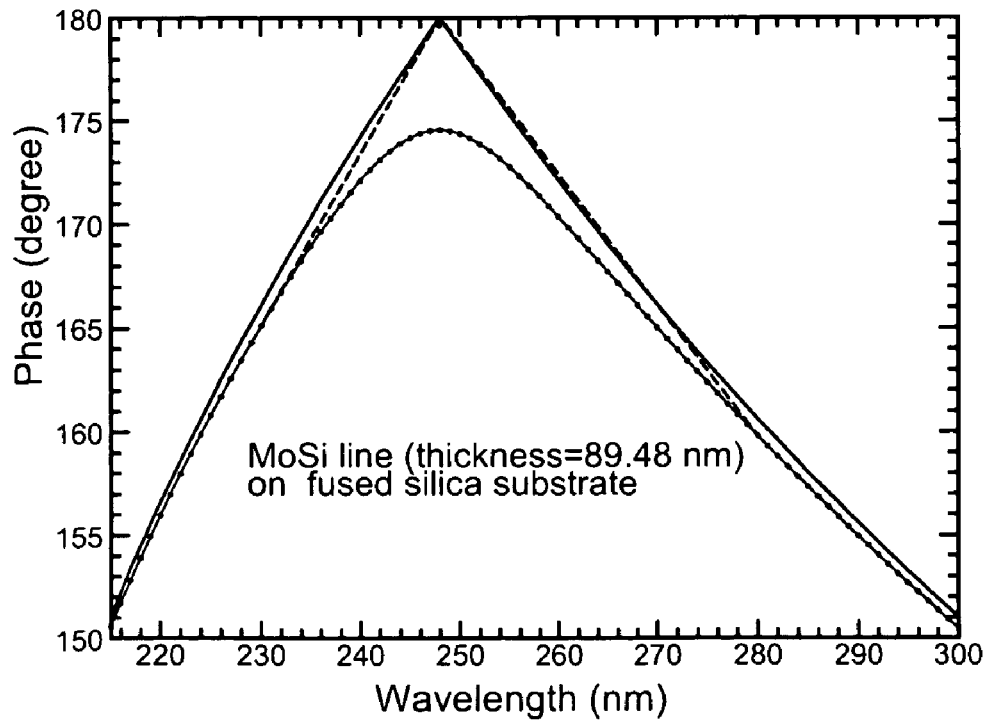
FIG. 24 shows direct phase estimates compared to the exact phase vs. wavelength for the example of FIG. 23.

FIG. 24 shows the approximate direct phase measurement (line with dots) compared to the exact phase (solid line) for the example of FIG. 23. The interpolation correction is shown with dashed lines. Here $\lambda_l$ and $\lambda_r$ are 230 nm and 280 nm respectively. In this case as well, the interpolation correction significantly improves accuracy near the 180 degree point.

Figure 25:
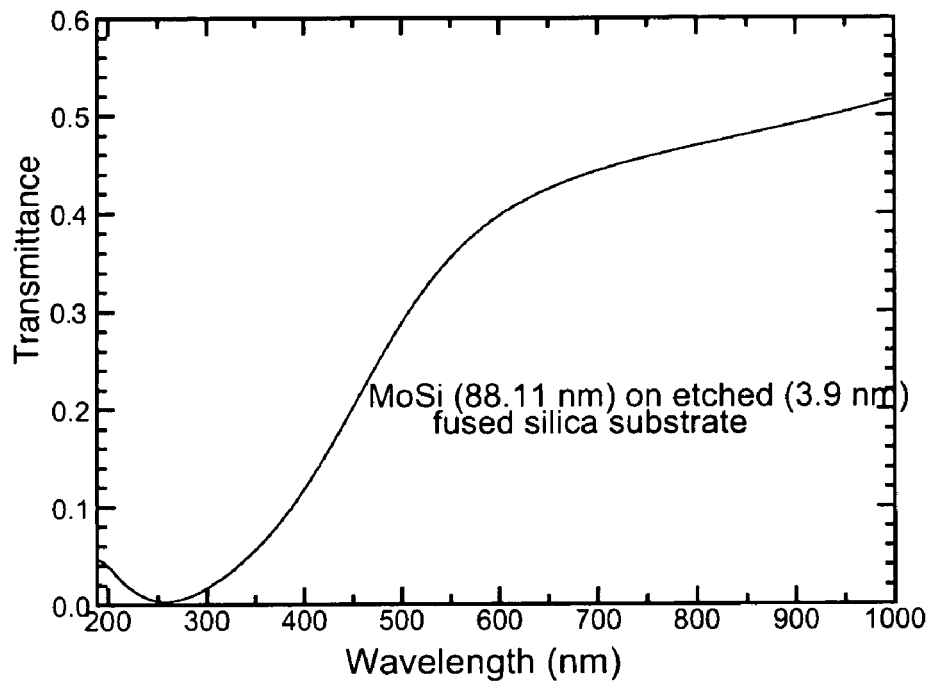
FIG. 25 shows transmittance vs. wavelength for a 88.11 nm deep MoSi line on a fused silica substrate with an additional 3.9 nm etch into the substrate.
Figure 26:
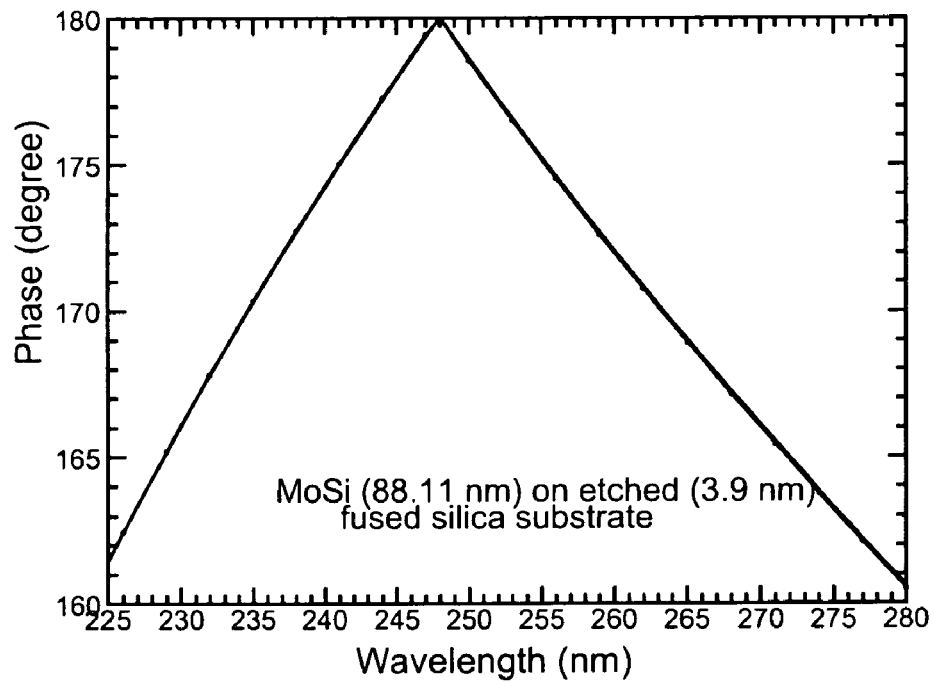
FIG. 26 shows direct phase estimates compared to the exact phase vs. wavelength for the example of FIG. 23.

In practice, phase shift masks of the type shown in FIG. 23 and FIG. 24 can have an approximately 177 degree contribution (at the wavelength of operation) from a MoSi absorber layer, and an additional 3 degrees of phase shift from a shallow etch into the substrate. FIG. 25 shows transmittance vs. wavelength for a phase shift mask having MoSi lines on a fused silica substrate where the line to space ratio is again 3:1. In this fourth example, the MoSi thickness is 88.11 nm and the fused silica space is etched an additional 3.9 nm. FIG. 26 shows the approximate direct phase shift measurement (line with dots) compared to the exact phase (solid line) for the example of FIG. 25. For this example, a different approximation is employed to obtain phase estimates. More specifically, a correction factor |C| is selected such that the quantity $$\frac{T_C - a_1^2 T_1 - a_2^2 T_2}{2 a_1 a_2 |C| \sqrt{T_1 T_2}}$$

has a value of −1 at a local minimum as a function of wavelength. The correction factor |C| thus determined is used in Eq. 37a to determine the phase. The motivation for this approach is as given above (i.e., the phase should reach exactly 180 degrees as the wavelength varies). This approach works particularly well for MoSi-type phase shift masks. Other phase estimation approaches (e.g., based on Eq. 38 and/or making use of interpolation as shown on FIG. 20c) are also applicable for this example.

It is also possible to estimate the complex correction factor C using Eq. 36 directly by using additional backside reflectance measurements, especially if the incident backside light is focused either on the front or back of the substrate so that multiple reflection effects are minimized. In this case, $r_{1,sa}^2$ and $r_{2,sa}^2$ are determined from backside reflectance with the beam focused on the front side (side a) from areas 1 and 2, and $r_{1,sb}^2$ and $r_{2,sb}^2$ are determined from backside (side b) reflectance with the beam focused on the back side (side b). The quantities $r_{1,sa} \cdot r_{2,sa}^*$ and $r_{1,sb} \cdot r_{2,sb}^*$ in the denominator can be determined from a backside reflectance measurement of the phase shifting features (1708 in FIG. 17) themselves. More specifically, Eq. 12 can be solved for its cross term as a function of measured parameters $R_1$, $R_2$ and $R_C$. In this approach, low loss in the substrate (i.e., $\exp(-2\alpha d) \approx 1$) is typically assumed.

Another aspect of the present invention is the optical measurement of lateral feature dimensions (e.g., critical dimensions). For example, consider a region three having area fractions $a_{31}$ and $a_{32}$ of features 1 and 2 and a region four having area fractions $a_{41}$ and $a_{42}$ of features 1 and 2. Since the left side of Eq. 37b does not depend on area fraction, the right side of Eq. 37b is the same for regions three and four. More specifically, we have $$\frac{T_{C3} - a_{31}^2 T_1 - a_{32}^2 T_2}{a_{31} a_{32}} = \frac{T_{C4} - a_{41}^2 T_1 - a_{42}^2 T_2}{a_{41} a_{42}}, \qquad \text{Eq. 41}$$

where $T_{C3}$ and $T_{C4}$ are the measured transmittances of regions three and four respectively. Furthermore, Eq. 41 will hold at any wavelength. Thus if measurements are made at m wavelengths, these m measurements can be used to determine the parameters $a_{31}$, $a_{32}$, $a_{41}$, and $a_{42}$. A suitable method for this determination is the nonlinear function minimization method as described in Chapter 14 of Press et al., "Numerical Recipes", 1989. The number of measurements m should be greater than or equal to the number of independent parameters to be determined. Thus in the typical case where $a_{32}=1-a_3$ and $a_{42}=1-a_4'$, we have m≧2. In cases where the pitch is known, determination of area fraction provides feature lateral size information (e.g., line width).

The direct phase measurement provided by the present invention is generally simpler and less costly to implement than prior art phase measurement approaches. Such prior art approaches include interferometry as in U.S. Pat. No. 6,122,056, reflectance modeling as in U.S. Pat. No. 5,087,121, and application of a phase shift to the incident light beam as in U.S. Pat. No. 5,604,591 and U.S. Pat. No. 5,392,116. Another example of an interferometry approach for direct phase measurement is considered by Kusunose et al., "Development of Phase-shift and Transmittance Metrology System for 157 nm PSMs", Proc. SPIE 5256, pp 628-637, 2003.

The preceding examples of direct phase measurement assume lateral coherence. In some cases, lateral coherence may be partial or even absent. Direct measurement of the phase according to the invention is applicable to the partially coherent case. More specifically, Eq. 35 and the following results can be modified to account for partial coherence according to partial coherence models known in the art. This consideration is relevant for sample design. Samples having features with excessively small lateral dimensions will have responses which are undesirably affected by diffraction. Samples having features with excessively large lateral dimensions may have responses which are undesirably complicated by less than complete lateral coherence. In addition, large lateral characterization features can undesirably reduce useful device area on a semiconductor chip. Selection of sample feature size in view of these considerations can be guided by experiment and/or by modeling, and can be done by one of ordinary skill in the art.

In view of the above, it will be clear to one skilled in the art that the above embodiments may be altered in many ways without departing from the scope of the invention. Accordingly, the scope of the invention should be determined by the following claims and their legal equivalents.

What is claimed is:

1. A method for determining a physical parameter of features on a substrate, said method comprising:
 a) illuminating said substrate with an incident light having an incident wavelength range $\Delta\lambda$ within which said substrate is at least semi-transparent such that said incident light enters said substrate and said features;
 b) receiving a response light from said substrate and said features;
 c) measuring a response spectrum of said response light;
 d) computing a complex-valued response due to said features and said substrate;
 e) determining said physical parameter from said response spectrum and said complex-valued response;
 f) providing said determined physical parameter as an output;
wherein said physical parameter is a relative transmission phase $\phi(\lambda)$ between a first part of said features and a second part of said features.

2. The method of claim 1, wherein said response light includes first light transmitted through said first part, second light transmitted through said second part, and third light transmitted through a third part of said features, and wherein a fraction $a_1$ of said third part is similar to said first part and a fraction $a_2$ of said third part is similar to said second part.

3. The method of claim 2, wherein said determining said physical parameter comprises:
 measuring a transmittance $T_1$ of said first part;
 measuring a transmittance $T_2$ of said second part;
 measuring a transmittance $T_C$ of said third part;
 determining an estimate of said phase $\phi(\lambda)$ according to $$\phi(\lambda) = \cos^{-1}\left(\frac{T_C - a_1^2 T_1 - a_2^2 T_2}{2 a_1 a_2 \sqrt{T_1 T_2}}\right).$$

4. The method of claim 2, wherein said determining said physical parameter comprises:
 measuring a transmittance $T_1$ of said first part;
 measuring a transmittance $T_2$ of said second part;
 measuring a transmittance $T_C$ of said third part;
 estimating a correction factor $|C|$ by adjusting $|C|$ such that $$\frac{T_C - a_1^2 T_1 - a_2^2 T_2}{2 a_1 a_2 |C| \sqrt{T_1 T_2}}$$

has a value of −1 at a local minimum with respect to wavelength;
 determining an estimate of said phase $\phi(\lambda)$ according to $$\phi(\lambda) = \cos^{-1}\left(\frac{T_C - a_1^2 T_1 - a_2^2 T_2}{2 a_1 a_2 |C| \sqrt{T_1 T_2}}\right).$$

5. The method of claim 2, wherein said determining said physical parameter comprises:
 measuring a transmittance $T_1$ of said first part;
 measuring a transmittance $T_2$ of said second part;
 measuring a transmittance $T_C$ of said third part;
 estimating a correction factor C from reflectance measurements;
 determining an estimate of said phase $\phi(\lambda)$ according to $$\phi(\lambda) = \cos^{-1}\left(\frac{T_C - a_1^2 T_1 - a_2^2 T_2}{2 a_1 a_2 |C| \sqrt{T_1 T_2}}\right).$$

6. The method of claim 5, wherein said substrate has an interface (sa) facing toward said incident light and an interface (sb) facing away from said incident light, and wherein said reflectance measurements comprise measurements of reflectances $|r_{1,sa}^2|$, $|r_{2,sa}^2|$, $|r_{1,sb}^2|$, $|r_{2,sb}^2|$ and of cross terms $r_{1,sa} r_{2,sa}^*$ and $r_{1,sb} r_{2,sb}^*$, and wherein said correction factor C is calculated from $$C = \frac{\sqrt{[1 - |r_{1,sa}^2 \cdot r_{1,sb}^2|] \cdot [1 - |r_{2,sa}^2 \cdot r_{2,sb}^2|]}}{1 - r_{1,sa} \cdot r_{2,sa}^* \cdot r_{1,sb} \cdot r_{2,sb}^*}.$$

7. The method of claim 1, wherein said determining said physical parameter further comprises:
 locating a wavelength $\lambda_m$ at which said phase $\phi(\lambda)$ has a local maximum near 180 degrees;
 determining a point $P_l$ having a wavelength $\lambda_l < \lambda_m$ and a phase of $\phi(\lambda_l)$;

determining a point $P_r$ having a wavelength $\lambda_r > \lambda_m$ and a phase of $\phi(\lambda_r)$;

determining a point $P_x$ having a wavelength $\lambda_m$ and a phase of 180 degrees;

correcting said phase $\phi(\lambda)$ by interpolating between points $P_l$ and $P_x$ for wavelengths between $\lambda_l$ and $\lambda_m$;

correcting said phase $\phi(\lambda)$ by interpolating between points $P_x$ and $P_r$ for wavelengths between $\lambda_m$ and $\lambda_r$.

8. The method of claim 1, wherein a refractive index of said features as a function of wavelength is calculated from said phase $\phi(\lambda)$.

9. The method of claim 1, wherein a thickness of said features is calculated from said phase $\phi(\lambda)$.

10. A method for determining a physical parameter of features on a substrate, said method comprising:
   a) illuminating said substrate with an incident light having an incident wavelength range $\Delta\lambda$ within which said substrate is at least semi-transparent such that said incident light enters said substrate and said features;
   b) receiving a response light from said substrate and said features;
   c) measuring a response spectrum of said response light;
   d) computing a complex-valued response due to said features and said substrate;
   e) determining said physical parameter from said response spectrum and said complex-valued response;
   f) providing said determined physical parameter as an output;
wherein said response light includes first light from a first part of said features, second light from a second part of said features, and third light from a third part of said features, and wherein a fraction $a_{31}$ of said third part is similar to said first part and a fraction $a_{32}$ of said third part is similar to said second part.

11. The method of claim 10 wherein said response light includes fourth light from a fourth part of said features, wherein a fraction $a_{41}$ of said fourth part is similar to said first part and a fraction $a_{42}$ of said fourth part is similar to said second part.

12. The method of claim 11, wherein said fractions $a_{31}$, $a_{32}$, $a_{41}$, and $a_{42}$ are determined by a method comprising:
   measuring a transmittance $T_1$ of said first part;
   measuring a transmittance $T_2$ of said second part;
   measuring a transmittance $T_{C3}$ of said third part;
   measuring a transmittance $T_{C4}$ of said fourth part;
   estimating $a_{31}$, $a_{32}$, $a_{41}$, and $a_{42}$ by fitting a model $$\frac{T_{C3} - a_{31}^2 T_1 - a_{32}^2 T_2}{a_{31} a_{32}} = \frac{T_{C4} - a_{41}^2 T_1 - a_{42}^2 T_2}{a_{41} a_{42}}$$

to measured data at two or more wavelengths.

13. An apparatus for determining a physical parameter of features on a substrate, said apparatus comprising:
   a) an illumination source for producing an incident light having an incident wavelength range $\Delta\lambda$ within which said substrate is at least semi-transparent;
   b) optics for guiding said incident light such that said incident light enters said substrate and said features;
   c) a detector for receiving a response light from said substrate and said features and measuring a measured response spectrum of said response light;
   d) a processing unit for computing a complex-valued response of said features and said substrate and for determining said physical parameter from said measured response spectrum and said complex-valued response;
wherein said physical parameter is a relative transmission phase $\phi(\lambda)$ between a first part of said features and a second part of said features.

14. The apparatus of claim 13, wherein said response light includes first light transmitted through said first part, second light transmitted through said second part, and third light transmitted through a third part of said features, and wherein a fraction $a_1$ of said third part is similar to said first part and a fraction $a_2$ of said third part is similar to said second part.

15. The apparatus of claim 14, wherein said determining said physical parameter comprises:
   measuring a transmittance $T_1$ of said first part;
   measuring a transmittance $T_2$ of said second part;
   measuring a transmittance $T_C$ of said third part;
   determining an estimate of said phase $\phi(\lambda)$ according to $$\phi(\lambda) = \cos^{-1}\left(\frac{T_C - a_1^2 T_1 - a_2^2 T_2}{2 a_1 a_2 \sqrt{T_1 T_2}}\right).$$

16. The apparatus of claim 14, wherein said determining said physical parameter comprises:
   measuring a transmittance $T_1$ of said first part;
   measuring a transmittance $T_2$ of said second part;
   measuring a transmittance $T_C$ of said third part;
   estimating a correction factor $|C|$ by adjusting $|C|$ such that $$\frac{T_C - a_1^2 T_1 - a_2^2 T_2}{2 a_1 a_2 |C| \sqrt{T_1 T_2}}$$

has a value of $-1$ at a local minimum with respect to wavelength;
   determining an estimate of said phase $\phi(\lambda)$ according to $$\phi(\lambda) = \cos^{-1}\left(\frac{T_C - a_1^2 T_1 - a_2^2 T_2}{2 a_1 a_2 |C| \sqrt{T_1 T_2}}\right).$$

17. The apparatus of claim 14, wherein said determining said physical parameter comprises:
   measuring a transmittance $T_1$ of said first part;
   measuring a transmittance $T_2$ of said second part;
   measuring a transmittance $T_C$ of said third part;
   estimating a correction factor C from reflectance measurements;
   determining an estimate of said phase $\phi(\lambda)$ according to $$\phi(\lambda) = \cos^{-1}\left(\frac{T_C - a_1^2 T_1 - a_2^2 T_2}{2 a_1 a_2 |C| \sqrt{T_1 T_2}}\right).$$

18. The apparatus of claim 17, wherein said substrate has an interface (sa) facing toward said incident light and an interface (sb) facing away from said incident light, and wherein said reflectance measurements comprise measurements of reflectances $|r_{1,sa}|^2$, $|r_{2,sa}|^2$, $|r_{1,sb}|^2$, $|r_{2,sb}|^2$ and of cross terms $r_{1,sa} r_{2,sa}^*$ and $r_{1,sb} r_{2,sb}^*$, and wherein said correction factor C is calculated from $$C = \frac{\sqrt{[1 - |r_{1,sa}^2 \cdot r_{1,sb}^2|] \cdot [1 - |r_{2,sa}^2 \cdot r_{2,sb}^2|]}}{1 - r_{1,sa} \cdot r_{2,sa}^* \cdot r_{1,sb} \cdot r_{2,sb}^*}.$$

19. The apparatus of claim 13, wherein said determining said physical parameter further comprises:
   locating a wavelength $\lambda_m$ at which said phase $\phi(\lambda)$ has a local maximum near 180 degrees;
   determining a point $P_l$ having a wavelength $\lambda_l < \lambda_m$ and a phase of $\phi(\lambda_l)$;
   determining a point $P_r$ having a wavelength $\lambda_r > \lambda_m$ and a phase of $\phi(\lambda_r)$;
   determining a point $P_x$ having a wavelength $\lambda_m$ and a phase of 180 degrees;
   correcting said phase $\phi(\lambda)$ by interpolating between points $P_l$ and $P_x$ for wavelengths between $\lambda_l$ and $\lambda_m$;
   correcting said phase $\phi(\lambda)$ by interpolating between points $P_x$ and $P_r$ for wavelengths between $\lambda_m$ and $\lambda_r$.

20. The apparatus of claim 13, wherein a refractive index of said features as a function of wavelength is calculated from said phase $\phi(\lambda)$.

21. The apparatus of claim 13, wherein a thickness of said features is calculated from said phase $\phi(\lambda)$.

22. An apparatus for determining a physical parameter of features on a substrate, said apparatus comprising:
   a) an illumination source for producing an incident light having an incident wavelength range $\Delta\lambda$ within which said substrate is at least semi-transparent;
   b) optics for guiding said incident light such that said incident light enters said substrate and said features;
   c) a detector for receiving a response light from said substrate and said features and measuring a measured response spectrum of said response light;
   d) a processing unit for computing a complex-valued response of said features and said substrate and for determining said physical parameter from said measured response spectrum and said complex-valued response;

wherein said response light includes first light from a first part of said features, second light from a second part of said features, and third light from a third part of said features, and wherein a fraction $a_{31}$ of said third part is similar to said first part and a fraction $a_{32}$ of said third part is similar to said second part.

23. The apparatus of claim 22 wherein said response light includes fourth light from a fourth part of said features, wherein a fraction $a_{41}$ of said fourth part is similar to said first part and a fraction $a_{42}$ of said fourth part is similar to said second part.

24. The apparatus of claim 23, wherein said fractions $a_{31}$, $a_{32}$, $a_{41}$, and $a_{42}$ are determined by a method comprising:
   measuring a transmittance $T_1$ of said first part;
   measuring a transmittance $T_2$ of said second part;
   measuring a transmittance $T_{C3}$ of said third part;
   measuring a transmittance $T_{C4}$ of said fourth part;
   estimating $a_{31}$, $a_{32}$, $a_{41}$, and $a_{42}$ by fitting a model $$\frac{T_{C3} - a_{31}^2 T_1 - a_{32}^2 T_2}{a_{31} a_{32}} = \frac{T_{C4} - a_{41}^2 T_1 - a_{42}^2 T_2}{a_{41} a_{42}}$$

to measured data at two or more wavelengths.

\* \* \* \* \*